United States Patent
Ando et al.

(10) Patent No.: US 7,936,939 B2
(45) Date of Patent: May 3, 2011

(54) MICROINJECTION APPARATUS AND AUTOMATIC FOCAL POINT ADJUSTMENT METHOD

(75) Inventors: Moritoshi Ando, Kawasaki (JP); Sachihiro Youoku, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1098 days.

(21) Appl. No.: 11/600,815

(22) Filed: Nov. 17, 2006

(65) Prior Publication Data

US 2008/0002868 A1 Jan. 3, 2008

(30) Foreign Application Priority Data

Jun. 29, 2006 (JP) .................................. 2006-179705

(51) Int. Cl.
G06K 9/00 (2006.01)
G06K 9/40 (2006.01)
C12M 3/00 (2006.01)
(52) U.S. Cl. ...... 382/255; 382/133; 382/152; 435/286.2
(58) Field of Classification Search .................. 382/100, 382/128–133, 152, 255; 435/286.2; 345/418, 345/419; 703/11; 348/95
See application file for complete search history.

(56) References Cited

U.S. PATENT DOCUMENTS

| | | | | |
|---|---|---|---|---|
| 2,472,907 | A * | 6/1949 | Kolesnikoff | 355/62 |
| 4,631,581 | A | 12/1986 | Carlsson | |
| 5,694,478 | A * | 12/1997 | Braier et al. | 382/133 |
| 6,593,129 | B1 * | 7/2003 | Takeshita et al. | 435/285.1 |
| 6,845,177 | B2 * | 1/2005 | Chiu | 382/199 |
| 7,050,613 | B2 * | 5/2006 | Murao et al. | 382/128 |
| 7,479,388 | B2 * | 1/2009 | Ando | 435/285.1 |
| 2002/0001402 | A1 * | 1/2002 | Berliner | 382/133 |
| 2002/0181784 | A1 * | 12/2002 | Shiratani | 382/218 |
| 2003/0082818 | A1 * | 5/2003 | Bahnson et al. | 436/63 |
| 2003/0179916 | A1 * | 9/2003 | Magnuson et al. | 382/128 |
| 2004/0106189 | A1 * | 6/2004 | Dodgson et al. | 435/285.2 |
| 2004/0161143 | A1 * | 8/2004 | Dietz et al. | 382/133 |
| 2004/0235143 | A1 * | 11/2004 | Sasaki et al. | 435/285.1 |
| 2005/0163359 | A1 * | 7/2005 | Murao et al. | 382/128 |
| 2005/0244948 | A1 * | 11/2005 | Ando | 435/285.1 |
| 2006/0024812 | A1 * | 2/2006 | Youoku et al. | 435/285.1 |

(Continued)

FOREIGN PATENT DOCUMENTS

DE 197 21 084 11/1998

(Continued)

OTHER PUBLICATIONS

Kirk J. Czymmek et al., "Confocal Microscopy in Mycological Research", Experimental Mycology, Academic Press, London, GB, vol. 18, No. 4, December 1994, pp. 278-281.

(Continued)

*Primary Examiner* — Bhavesh M Mehta
*Assistant Examiner* — Mia M Thomas
(74) *Attorney, Agent, or Firm* — Fujitsu Patent Center

(57) ABSTRACT

A microinjection apparatus, which injects an object into a cell with a needle, acquires a first image that is an image of the cell at a first focal position and a second image that is an image of the cell at a second focal position, and decides a state of the cell based on a difference image obtained from the first image and the second image. Execution of such sequence of processing makes it possible to measure a state of a cell without involving human work and confirm the state of the cell in performing a microinjection, without a necessity of experienced skill, efficiently, and simply.

12 Claims, 21 Drawing Sheets

U.S. PATENT DOCUMENTS

| | | | |
|---|---|---|---|
| 2006/0223163 A1* | 10/2006 | Sakai et al. | 435/285.1 |
| 2006/0228771 A1* | 10/2006 | Dodgson et al. | 435/30 |
| 2007/0149984 A1* | 6/2007 | Nishiyama et al. | 606/116 |
| 2007/0249038 A1* | 10/2007 | Adamo et al. | 435/287.1 |
| 2008/0063720 A1* | 3/2008 | Gounko et al. | 424/489 |
| 2008/0112606 A1* | 5/2008 | Lee et al. | 382/133 |
| 2008/0126051 A1* | 5/2008 | Ando et al. | 703/11 |
| 2008/0273786 A1* | 11/2008 | Komori et al. | 382/133 |

FOREIGN PATENT DOCUMENTS

| | | | |
|---|---|---|---|
| DE | 19721084 | * | 11/1998 |
| EP | 1 479 759 | | 11/2004 |
| EP | 1 595 941 | | 11/2005 |
| EP | 1 621 912 | | 2/2006 |
| JP | 2624719 | | 4/1997 |

OTHER PUBLICATIONS

Extended European Search Report, mailed Oct. 30, 2007 and issued in corresponding European Patent Application No. 06124425.7-1521.

\* cited by examiner

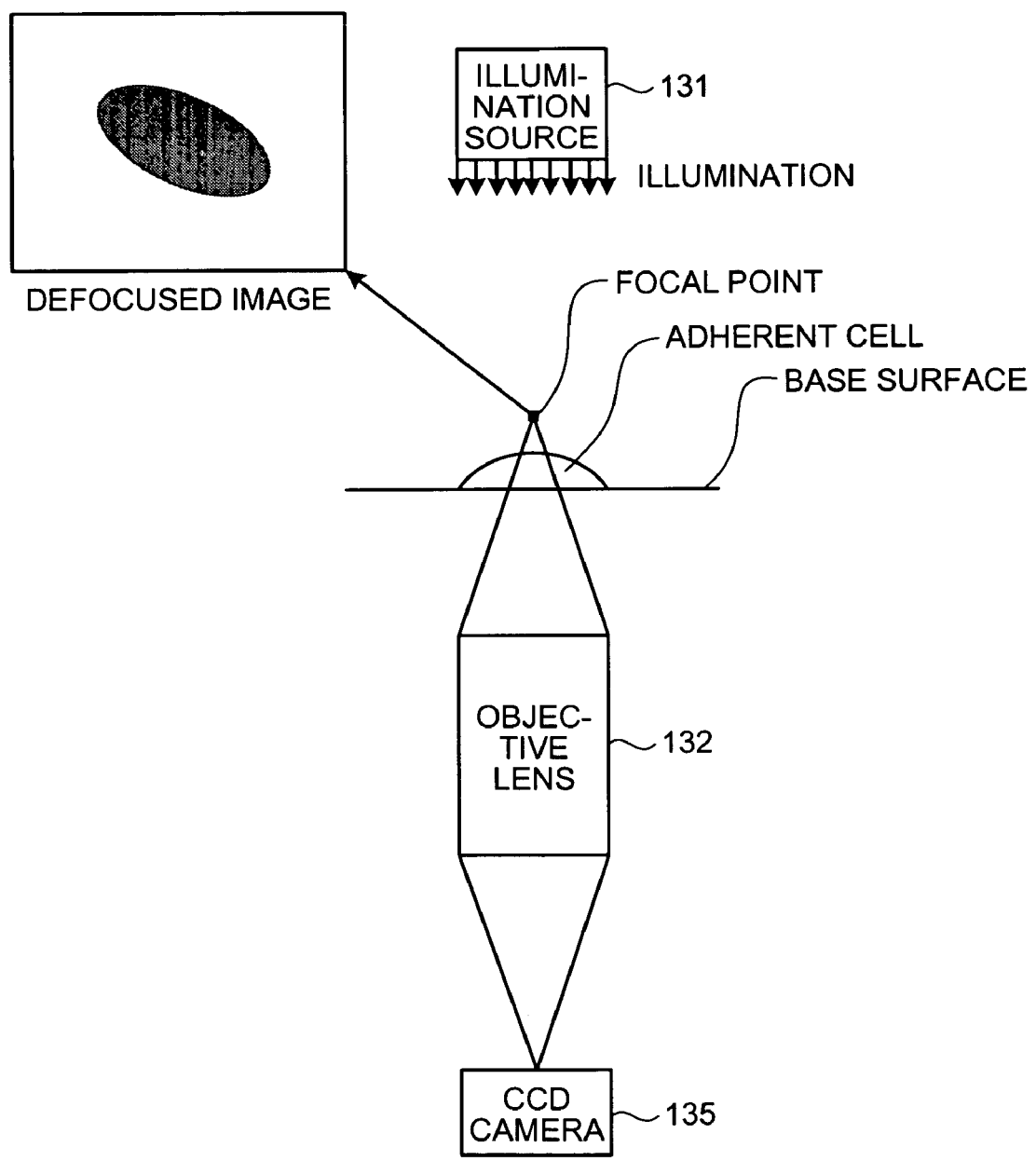

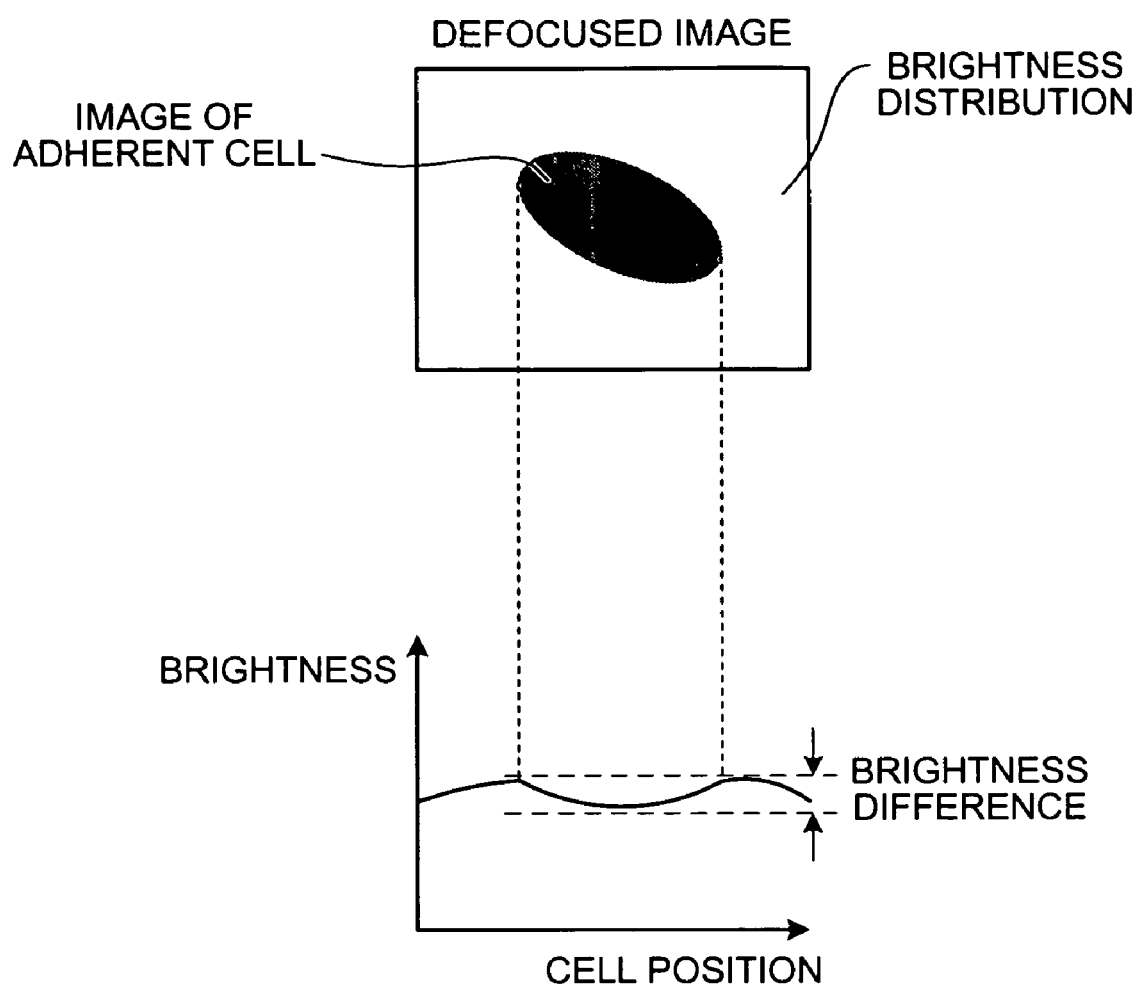

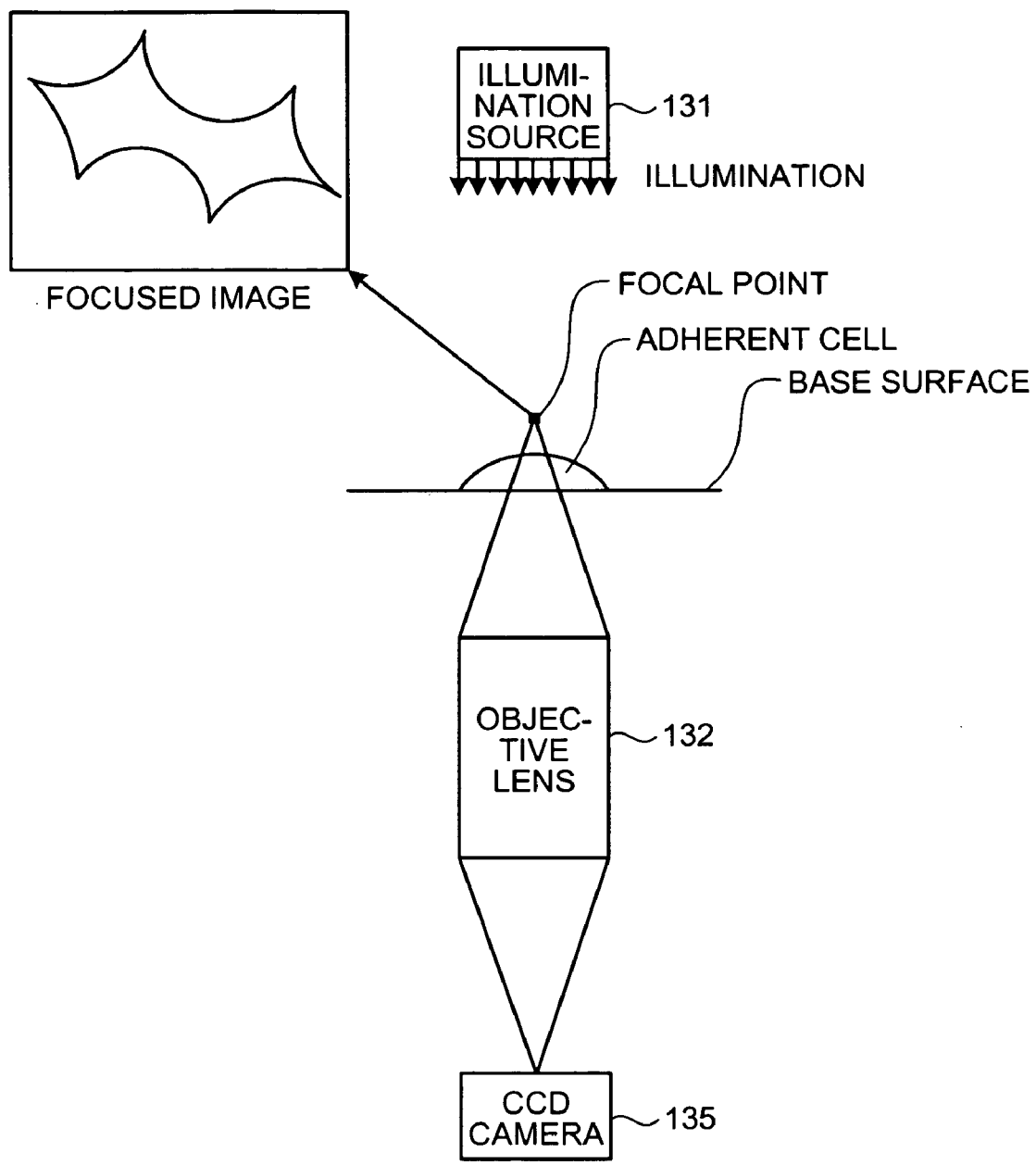

BOTTOM POSITION L'=|b|/(|a|+|b|)×L

DIFFERENTIAL AGGREGATE SMALL AT ONE SIDE

DIFFERENTIAL AGGREGATE MINIMUM VALUE IS ZERO

DEFOCUSED IMAGE

DEFOCUSED/BINARIZED

FOCUSED IMAGE

OVERLAPPING OF FOCUSED IMAGE AND DEFOCUSED IMAGE
(EDGE Δ10-20 μm)

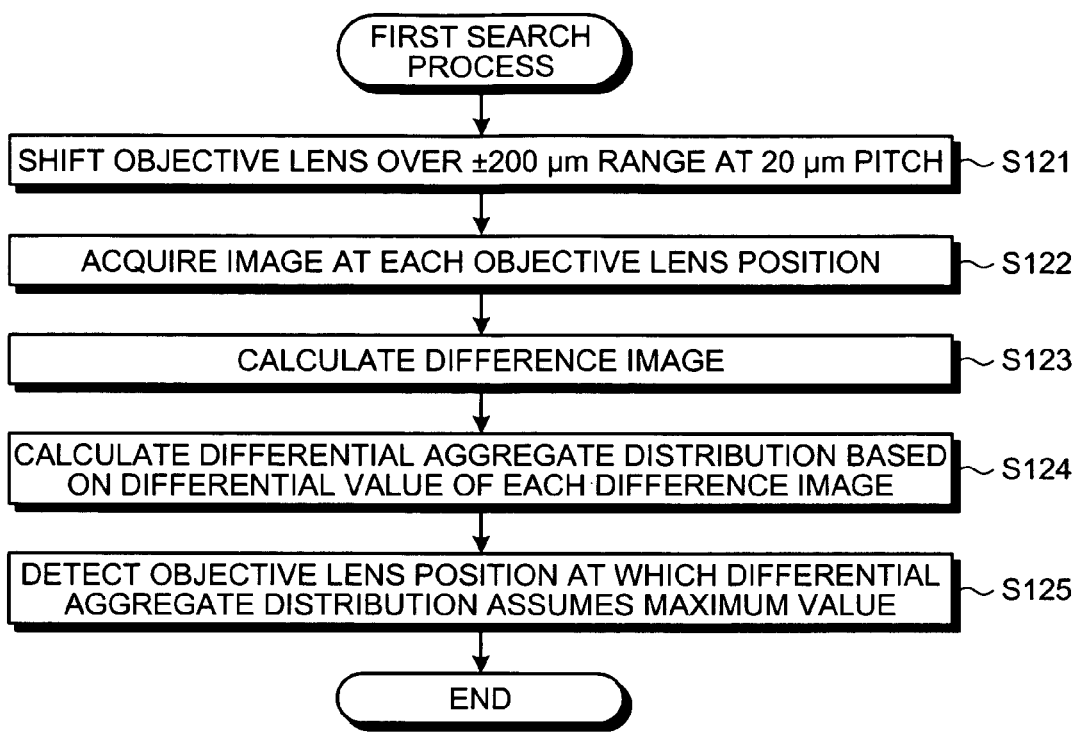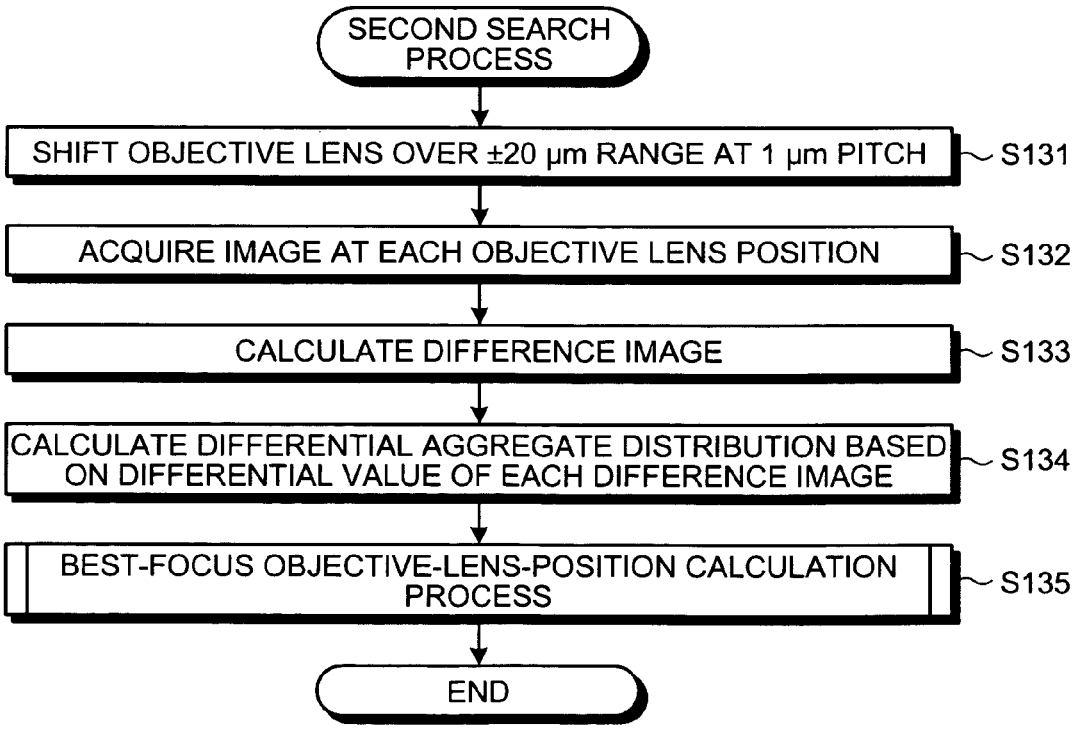

MICROINJECTION APPARATUS AND AUTOMATIC FOCAL POINT ADJUSTMENT METHOD

BACKGROUND OF THE INVENTION

1. Field of the Invention

The present invention relates to a technology for injecting an object into a cell with a needle.

2. Description of the Related Art

A study of an alteration of genetic information of a cell by running a microscopic needle into the cell and injecting a gene, using a microscope clarifies a role of the gene and permits a tailor-made medicine of conducting gene treatment in accordance with individual genetic characteristics. Such study has made it possible to cure illness attributable to genetic causes that have heretofore been incurable.

The methods for injecting a gene into the cell can be, e.g., an electric method (electroporation), a chemical method (lipofection), a biological method (vector method), a mechanical method (microinjection), etc.

Among those methods, the electrical method includes breaking the cell membrane by running a large current, giving a big damage to the cell. The chemical method is limited in the number of genes to be introduced and is poor in respect of introduction efficiency. The biological method has the defects such as that it there is a limitation on the number of materials to be introduced and that safety of this method cannot be confirmed.

As a result, at present, in many cases, the mechanical method is employed as the safest and the most efficient method. For example, Japanese Patent No. 2624719 discloses a technology regarding the microinjection apparatus that arranges cells in regular order and automatically performs the microinjection.

The conventional technology represented by the above-identified patent, however, has the following problems. A first problem is that an experienced skill is required for a gene injection work because, due to the transparency of a cell as an object and a petri dish to which the cell adheres, the presence itself of the cell is not clear and the cell itself must be detected and must be shifted to an observation position, or a height of the cell or a border between the cell and the petri dish are difficult to judge and that since, due to one objective lens used at a microscope, three-dimensional feeling of the cell and the petri dish is difficult to grasp, work must be performed by alternately using a low magnification lens and a high magnification lens, resulting in inefficiency.

A second problem is that due to an inclination of a bottom surface itself of a petri dish, an absolute position of the cell in vertical direction varies depending on the position at which gene injection work is carried out, and therefore, a focal position of a microscope must be adjusted and a needle position must be adjusted, each time, resulting in inefficiency. There was a further problem that since the thickness and the inclination of the bottom surface of the petri dish are not uniform, varying from one petri dish to another, and the thickness and the inclination of the petri dish vary depending on a way of arranging the petri dish on a microscope stage, the focal position of the microscope must be adjusted and the needle position must be adjusted each time the petri dish itself is changed for another one or the way of arranging the petri dish on the stage is changed.

As a result, a method of placing a mark on the petri dish or a method of having the cell adhere to a cell catching plate on which a grid is drawn and arranging it within the petri dish were conventionally in use as a method of measuring the bottom surface, but these methods had a problem of contaminating the cell in placing the mark on the petri dish or of taking much trouble in preparing samples.

To solve the second problem, a method was devised of measuring the bottom surface using a dedicated optical system different from a system of observing the cell, but this method had a problem that a microinjection apparatus must have at least two lines of optical system, making a configuration of the apparatus complicated, or making the apparatus expensive or reducing the usability and maintainability of the apparatus.

The method of observing the cell conventionally was a differential interference method and a phase difference contrast optical system, but these methods, developed for making the cell more easily viewable in visual observation, had a problem that an edge of the cell is overemphasized, and therefore, were not suitable for an automation of the cell focal point adjustment.

SUMMARY OF THE INVENTION

It is an object of the present invention to at least partially solve the problems in the conventional technology.

According to an aspect of the present invention, a microinjection apparatus that injects an object into a cell with a needle includes an image acquiring unit that acquires a first image that is an image of the cell at a first focal position and a second image that is an image of the cell at a second focal position; and a state deciding unit that decides a state of the cell based on a difference image obtained from the first image and the second image.

According to another aspect of the present invention, a method of automatically adjusting a focal point of a lens relative to a cell for injecting an object into the cell with a needle includes acquiring with an image acquiring unit a first image that is an image of the cell at a first focal position and a second image that is an image of the cell at a second focal position; and deciding a state of the cell based on a difference image obtained from the first image and the second image.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2A is an explanatory diagram for description of features of an automatic focal point adjustment method according to the first embodiment;

FIG. 2B is an explanatory diagram for description of features of an automatic focal point adjustment method according to the first embodiment;

FIG. 2C is an explanatory diagram for description of features of an automatic focal point adjustment method according to the first embodiment;

FIG. 14 is a flowchart of a procedure of the first search process;

FIG. 15 is a flowchart of a procedure of the second search process;

DETAILED DESCRIPTION OF THE PREFERRED EMBODIMENTS

Exemplary embodiments of the present invention will be explained below with reference to accompanying drawings.

The first embodiment relates to automatically measuring a focal point of an adherent cell in the microinjection apparatus equipped with an illumination source and a CCD camera for taking an image of the adherent cell arranged on a bottom surface of a petri dish through an objective lens of a microscope. The second embodiment relates to calculating an inclination of the bottom surface of the petri dish, based on focal positions of the adherent cell obtained at a plurality of observation positions, by applying the microinjection apparatus and the automatic focal point adjustment method shown in the first embodiment.

Figure 1:
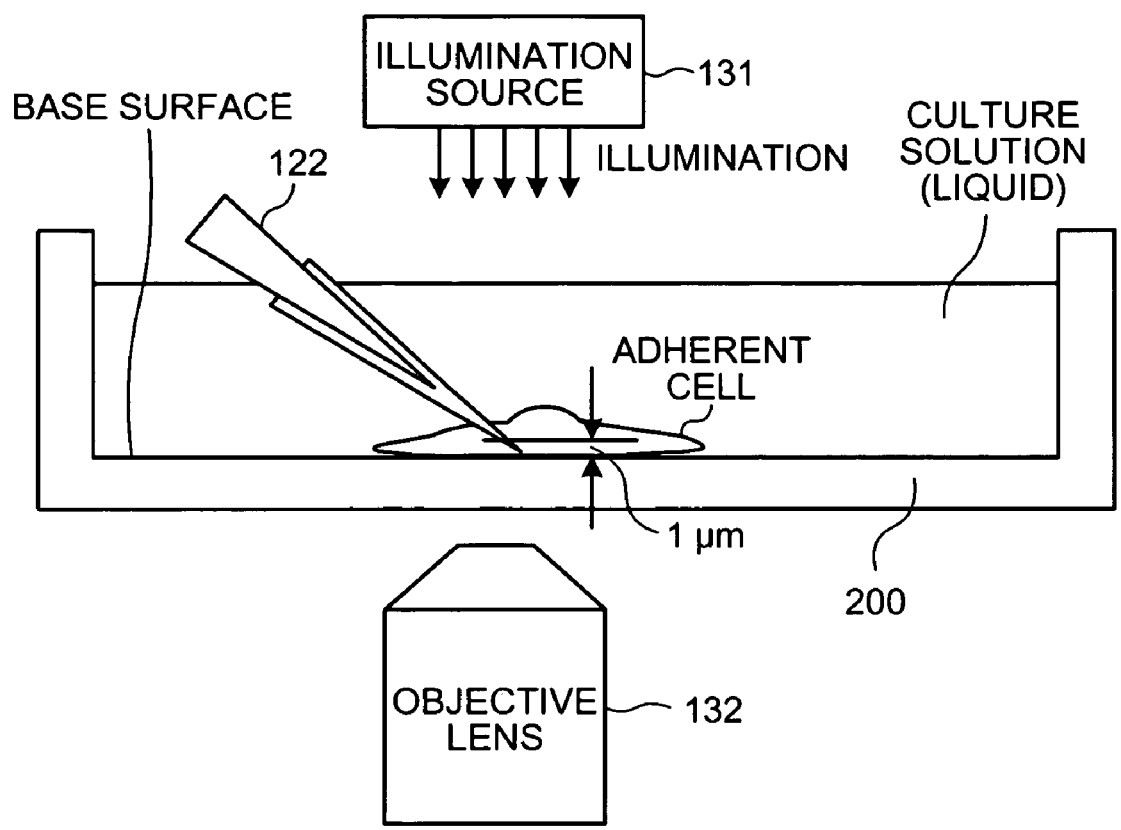
FIG. 1 is an explanatory diagram for description of the microinjection into an adherent cell.

FIG. 1 is a schematic for explaining the technique of microinjection into an adherent cell. An adherent cell is a cell that has a nature of adhering to other cells and, by concentration of same kind of cells, constitutes a part of a living organism. Thus, an adherent cell has the nature opposite to that of a non-adherent cell, or a floating cell, such as a red blood cell, which does not have the nature of adherence and functions floating alone.

As shown in FIG. 1, when performing microinjection into an adherent cell, the adherent cell is placed on the bottom surface of the petri dish 200 that is filled with fluid such as a culture solution. An illumination source 131 illuminates an area surrounding the adherent cell and an objective lens 132 arranged under the petri dish 200 obtains a magnified image of the adherent cell. In this state, a needle 122 is guided into the adherent cell making use of the magnified image of the adherent cell and an object present in the needle 122 is injected into the adherent cell. The object can be a gene.

A plate having minute holes can be provided on the bottom surface of the petri dish, and cells are captured in those minute holes, but in the following description, the case of not using the plate has been explained. Moreover, the bottom surface of the petri dish is referred to as a base surface.

The adherent cell is substantially flat on the bottom surface of the petri dish 200. In other words, while the cell has an area of 20 μm to 30 μm in the horizontal direction, it has a thickness of only 5 μm or so in the vertical direction. To puncture the adherent cell with the leading edge of the needle 122 and efficiently inject a gene into the adherent cell, the needle 122 is lowered at a high speed to a distance of around 1 μm above the base surface. To operate the needle 122 in this manner, i.e., without touching the base surface, requires high experience and skill.

The reason for such difficulty of the control of the needle 122 is that a border between the cell and the petri dish is not clear due to the transparency of the adherent cell and a transparent material making up the petri dish that has the adherent cell adhere to the bottom surface thereof and that a perspective and three-dimensional feeling is hard to grasp because observation is made basically using one objective lens only.

Adherent cells are present at random on the bottom surface of the petri dish 200 and therefore, even if a visual field of the objective lens 132 is fixed to a certain point of observation position, it is possible that no adherent cell at all is present within this visual field. It is also possible that it takes considerable times of trial and error and sometimes becomes very burdensome to make manual adjustments so that the adherent cell comes within the visual field of the objective lens, by shifting a position of the petri dish 200 or by shifting a position of the adherent cell itself. The present invention was conceived to solve these problems.

A microinjection apparatus and an automatic focal point adjustment method of the first embodiment will be explained with reference to FIGS. 2A to 16. Description will firstly be made of features of the automatic focal point adjustment method according to the first embodiment, with reference to FIGS. 2A to 2C. FIGS. 2A to 2C are explanatory diagrams for description of features of the automatic focal point adjustment method according to the first embodiment.

FIG. 2A shows a situation of obtaining a defocused image by setting a focal point of an objective lens relative to an adherent cell on a base surface to a position away from the adherent cell. As shown, an illumination is irradiated from the illumination source 131 arranged above an adherent cell adhering to the base surface to the adherent cell and a defocused image of the adherent cell is taken by a CCD camera 135 through the objective lens 132 arranged below the base surface.

Prior to this defocused image, a defocused image is taken with the focal point set 1 mm above the adherent cell. This is determined as a standard reference image. Though this reference image is considerably blurred as compared with the defocused image with the focal point set at a position close to an expected surface position of the adherent cell, these two defocused images have approximate distributions of intensity of light from the illumination source, and a height variation due to a slope of the base surface of the petri dish is 100 µm to 200 µm at best, small enough as compared with 1 mm, making no big difference to the image characteristics, and therefore, the reference image can be used as the reference image in respect of brightness of the image.

Next, a defocused image is taken with the focal point set at the focal position 200 µm above the adherent cell, and an image of difference from the reference image is obtained. Or, defocused images are taken with the focal point set at a plurality of different positions, at positions close to the expected surface position of the adherent cell, and images of difference from the reference image are obtained. A slice level determining a plurality of different positions for the focal point is to be a brightness value 10% to 20% smaller than that of the reference image.

As shown in FIG. 2B, out of the defocused image with the focal point set at the focal position 200 µm above the adherent cell or the defocused images taken at the slice level, the image in which the adherent cell is present has a region with a low brightness and a dark look as compared with a surrounding region. At a part where the adherent cell is not present, the brightness is little different from that of the reference image. Out of the difference images, the difference image in which the adherent cell is present is binarized. Digitizing is a processing of expressing an image in monochrome; the processing of converting each pixel to white if the brightness of such pixel is greater than a predetermined threshold and converting each pixel to black if the brightness of such pixel is smaller than the predetermined threshold.

Referring to the difference image with the binarized adherent cell, an area of a region whose brightness is lower than that of a surrounding region, and at the same time, the smallest brightness value in such region can be obtained. The lower brightness than that of a surrounding region unit that the brightness is smaller than a predetermined threshold. If a correlation between the area and the brightness is in a certain relationship, it can be judged that a normal adherent cell that can be an object of microinjection is present within the visual field of the objective lens in which the defocused image is taken.

Figure 3:
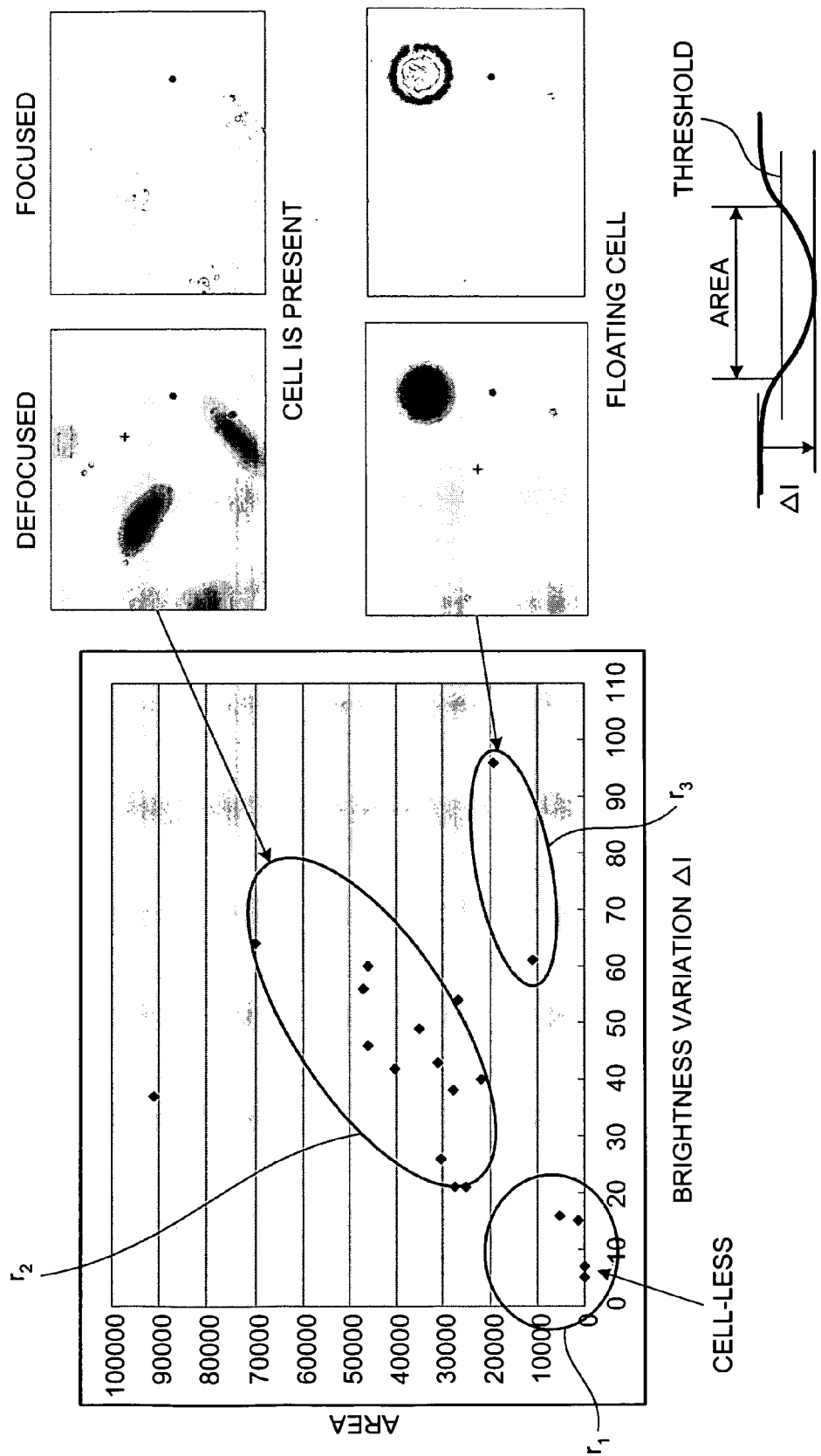
FIG. 3 is an explanatory diagram for schematic description of a cell state measurement in the automatic focal point adjustment method according to the first embodiment.

For example, in a graph of a correlation in FIG. 3, points specified by ΔI showing a degree of lowness of brightness from a standard, with the brightness of the reference image being taken as the standard, and by an area of the region whose brightness is lower than a predetermined threshold are plotted on a two-dimensional correlation graph. If a plotted point is present in the region illustrated as r1, then it can be judged that the adherent cell itself is not present within the visual field of the objective lens in which the defocused image is taken.

If a plotted point is present in the region illustrated as r2, then it can be judged that a normal adherent cell that can be an object of microinjection is present in moderate concentration within the visual field of the objective lens in which the defocused image is taken. If a plotted point is present in the region illustrated as r3, then it can be judged that since a normal adherent cell that can be an object of microinjection is present in a floating condition within the visual field of the objective lens in which the defocused image is taken, the adherent cell can not be used for the microinjection.

If it is not judged that a normal adherent cell that can be an object of microinjection is present within the visual field of the objective lens 132, then the focal point is shifted upward and downward several times at a comparatively coarse pitch of, for example, around 100 µm, and a judgment is made as to presence or absence of the normal adherent cell. If it is not judged that the normal adherent cell is present even by this method, then the observation position as the visual field of the objective lens 132 is shifted in horizontal direction, and such sequence of processing is performed again as shown in the above description of FIGS. 2A and 2B.

As shown in the description of FIG. 2B, if it is judged that the normal adherent cell that can be an object of the microinjection is present within the visual field of the objective lens 132 in which the defocused image was taken, then, as shown in FIG. 2C, images are detected while shifting the focal point upward and downward at the pitch of the order of 10 to 20 µm, difference images with the above-identified reference image are obtained, and a differential processing is applied to the difference images. The differential processing means a rate of change of the pixel value at each position within the image. The differential processing may be representative ones such as the Sobel processing.

Figure 4:
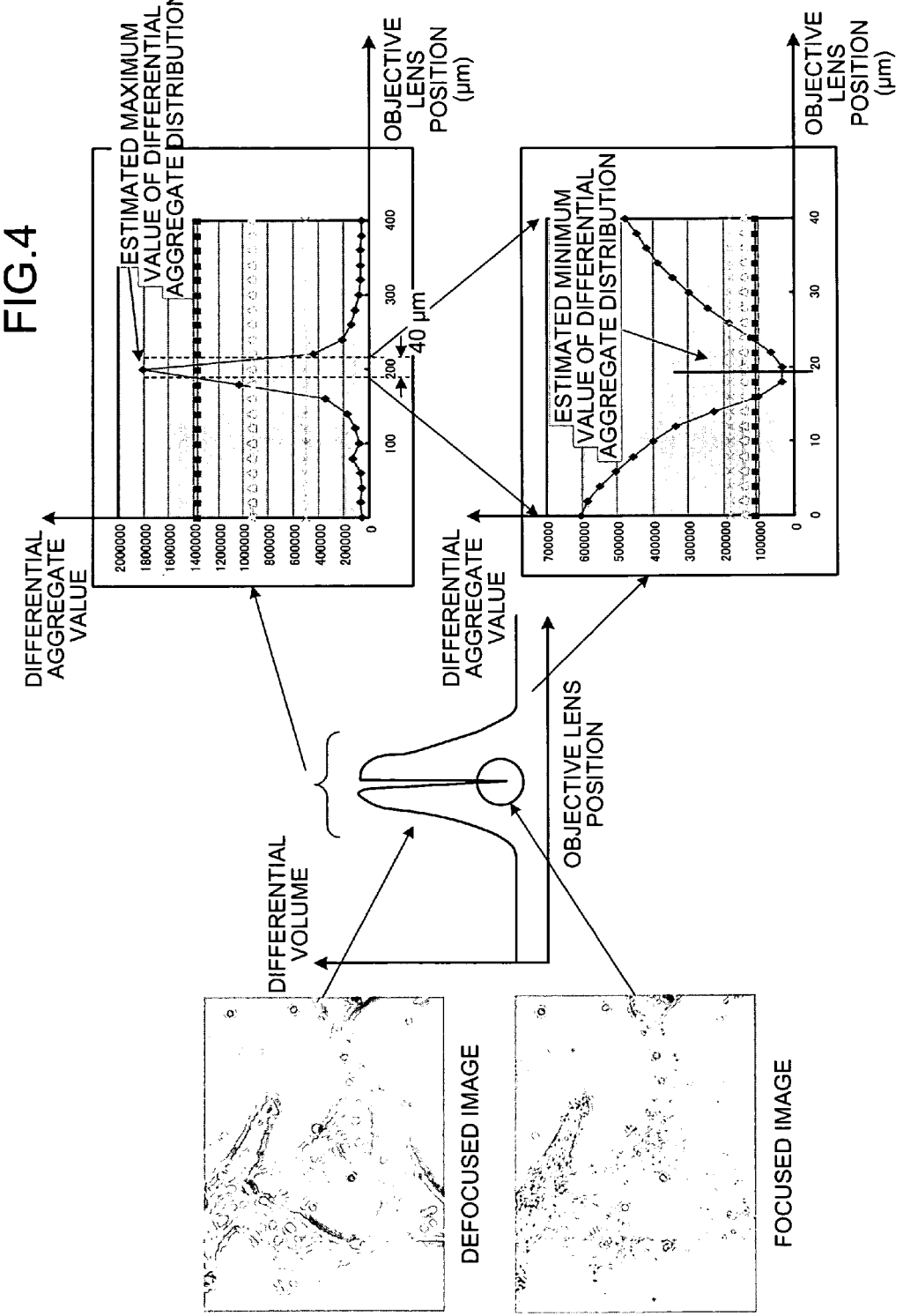
FIG. 4 is an explanatory diagram for schematic description of a cell focal position measurement in the automatic focal point adjustment method according to the first embodiment.

Next, a calculation is made of an aggregate of absolute values of differential values (differential aggregate) within the image, and a calculation is made of a distribution of the differential aggregate according to the focal position. Here, near a true focal point of the adherent cell, the differential aggregate assumes a maximum value macroscopically. Since the true focal point of the adherent cell is near the focal position at which the differential aggregate comes to its peak macroscopically (at the true focal point the differential value comes to its minimum), a calculation is made of a center of a curve of the differential aggregate distribution. In this manner, an estimated maximum value of the differential aggregate distribution is calculated (FIG. 4). As shown in FIG. 4, near the estimated maximum value of the differential aggregate distribution, a defocused image of the adherent cell can be obtained.

The focal position at which the differential aggregate distribution comes to its maximum macroscopically can be obtained by finding a peak of the differential aggregate distribution and calculating a center of the focal position represented by two points at the intersection of a straight line assuming a value lower than the peak by a predetermined value with the curve of the differential aggregate distribution. The above-mentioned straight line is referred to as a slice. Further calculation is made of a center of the focal position represented by two points at the intersection of a straight line assuming a value further lower by the same predetermined value with the curve of the differential aggregate distribution. By repeating this process of calculating intersection points from a slice and calculating a center of the intersection points a certain number of times, a plurality of centers of intersection points indicative of the focal positions are obtained, and an average thereof is considered as the focal position at which the differential aggregate comes to its peak (see FIG. 5).

Next, images of the adherent cell are taken while shifting the focal position upward and downward, for example, at 1 μm pitch, within the range of, for example, 20 μm upward and downward from the focal position at which the differential aggregate comes to its peak as obtained by the above-identified method, and a calculation is made of differential values of difference images with the above-identified reference image. Then, a calculation is made of an aggregate of absolute values of differential values (differential aggregate) of difference images at respective focal positions, and a calculation is made of a distribution of the differential aggregate according to focal positions. Near a true focal point of the adherent cell, the differential aggregate assumes a minimum value, microscopically. Since the focal position at which the differential aggregate comes to its minimum is the true focal point of the adherent cell, a calculation is made of a center of the curve of the differential aggregate distribution. In this manner, an estimated minimum value of the differential aggregate distribution is calculated (see FIG. 4). As shown in FIG. 4, a focused image of the adherent cell is obtained near the estimated minimum value of the differential aggregate distribution.

The focal position at which the differential aggregate distribution comes to its minimum microscopically is obtained based on gradients of two lines tangent to the curve of the differential aggregate distribution at two respective points at the intersection of a straight line upward offset by a predetermined value (herein, α) from the minimum value of the differential aggregate distribution with the curve of the differential aggregate distribution. Namely, a point at which a line segment that is cut off from the straight line upward offset by α from the minimum value of the differential aggregate distribution by the curve of the differential aggregate distribution is divided at a ratio of the gradients of the two tangent lines mentioned above is the focal position to be obtained (see FIG. 6).

Figure 6:
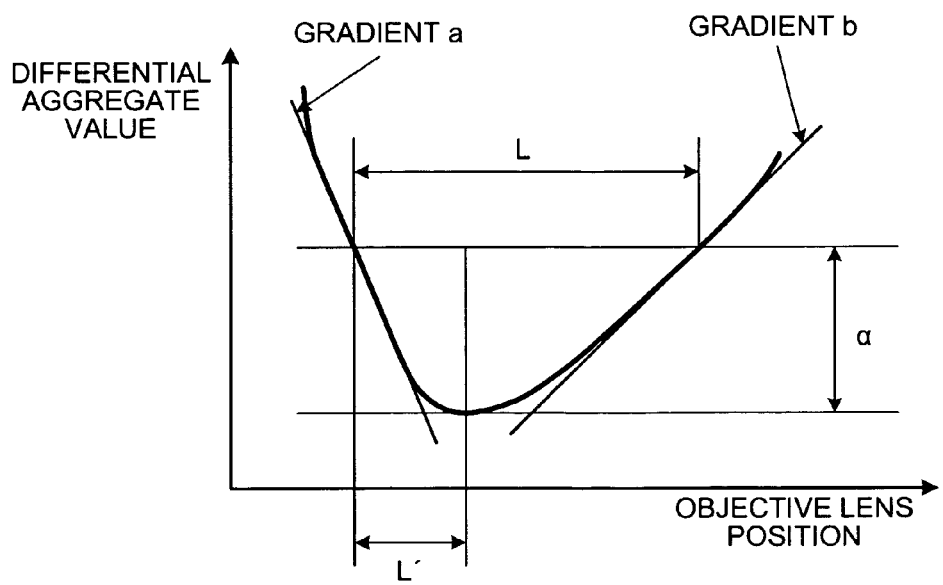
FIG. 6 is an explanatory diagram for schematic description of estimation of an objective lens position at which a differential aggregate comes to minimum in the automatic focal point adjustment method according to the first embodiment.

As shown in FIG. 6, if a length of the line segment cut off from the straight line upward offset by α from the minimum value of the differential aggregate distribution by the curve of the differential aggregate distribution is given as L, and a distance between the intersection point at which a value of an objective lens position is smaller, out of the two points at intersection of the straight line with the curve of the differential aggregate distribution, and a value of the objective lens position at which the differential aggregate distribution assumes the minimum value is given as L', then a relation of $L'=|b|/(|a|+|b|)\times L$ applies (|*| represents absolute value). Namely, the split ratio at which the line segment cut off from the straight line upward offset by α from the minimum value of the differential aggregate distribution by the curve of the differential aggregate distribution is divided by the value of the objective lens position at which the differential aggregate distribution assumes the minimum value is $|b|:|a|$.

As shown in FIG. 2C, at the obtained focal position, the image of the adherent cell becomes a focused image with the focal point corresponding to the bottom surface of the adherent cell. The focused image is obtained using a property that, in a microscope, at the focal position at which the differential aggregate distribution comes to its minimum, contents of the adherent cell such as a cell nucleus become least visible because the focal point corresponds to the bottom surface of the adherent cell. The focal position at which this focused image is obtained is the focal position at which a profile of the adherent cell can be grasped most clearly.

Figure 7A:
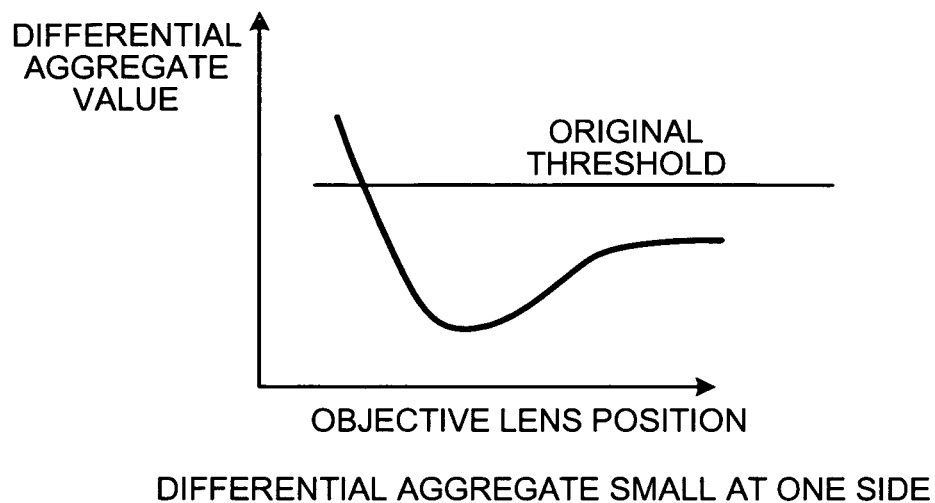
FIG. 7A is a diagram of an example of the differential aggregate distribution.
Figure 7B:
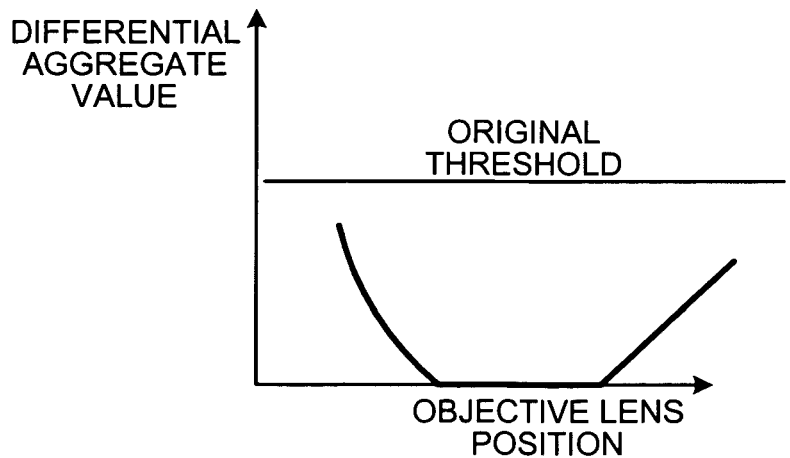
FIG. 7B is a diagram of an example of the differential aggregate distribution.

The method shown in FIG. 6 permits estimation of a value of the objective lens position at which the differential aggregate distribution assumes the minimum value even in the case of an asymmetric differential aggregate distribution in which the differential aggregate is comparatively small at one side of the range as shown in FIG. 7A or a differential aggregate distribution in which the minimum value of the differential aggregate distribution is zero over a certain section as shown in FIG. 7B. Needless to say, the value of the objective lens position at which the differential aggregate distribution assumes the minimum value can be estimated by the method shown in FIG. 6 even in a symmetric differential aggregate distribution. In this case, the center of symmetry is the value of the objective lens position at which the differential aggregate distribution assumes the minimum value.

Description will then be made of a processed image of a cell state measurement and a focal position measurement in the automatic focal point adjustment method according to the first embodiment. FIGS. 8A to 8D are diagrams of processed images of the cell state measurement and the focal position measurement in the automatic focal point adjustment method according to the first embodiment.

Figure 8A:
FIG. 8A is a diagram of a processed image of a cell state measurement and a focal position measurement in the automatic focal point adjustment method according to the first embodiment.
Figure 8B:
FIG. 8B is a diagram of a processed image of a cell state measurement and a focal position measurement in the automatic focal point adjustment method according to the first embodiment.
Figure 8C:
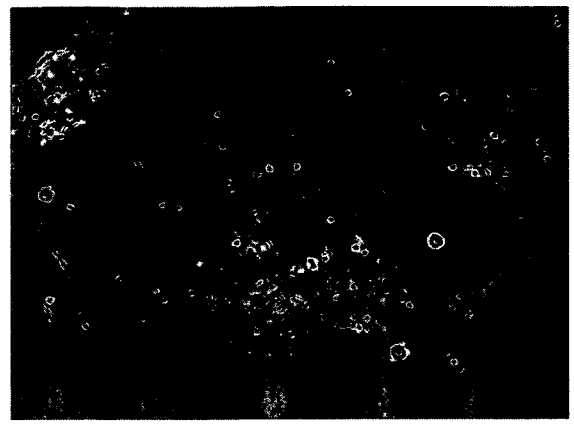
FIG. 8C is a diagram of a processed image of a cell state measurement and a focal position measurement in the automatic focal point adjustment method according to the first embodiment.
Figure 8D:
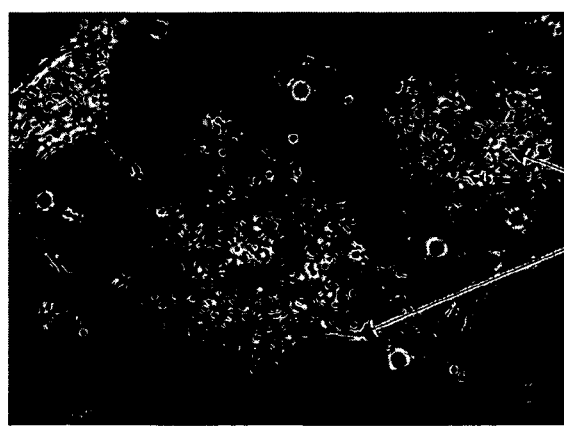
FIG. 8D is a diagram of a processed image of a cell state measurement and a focal position measurement in the automatic focal point adjustment method according to the first embodiment.

FIG. 8A is an example of a defocused image of the adherent cell obtained by setting the focal point 140 μm above the adherent cell. In the image of FIG. 8A, while presence of a cell nucleus can be confirmed, a profile of the adherent cell is not clear. Therefore, it can not be said that the adherent cell is clearly present within the image. FIG. 8B is an example of an image obtained by binarizing the defocused image of FIG. 8A. FIG. 8C is an example of a focused image, a bright-field image of the cell. FIG. 8D is an example of an overlapped image of the focused image and the defocused image. In FIG. 8D, the adherent cell having a clear profile and a cell nucleus can be recognized.

Figure 9:
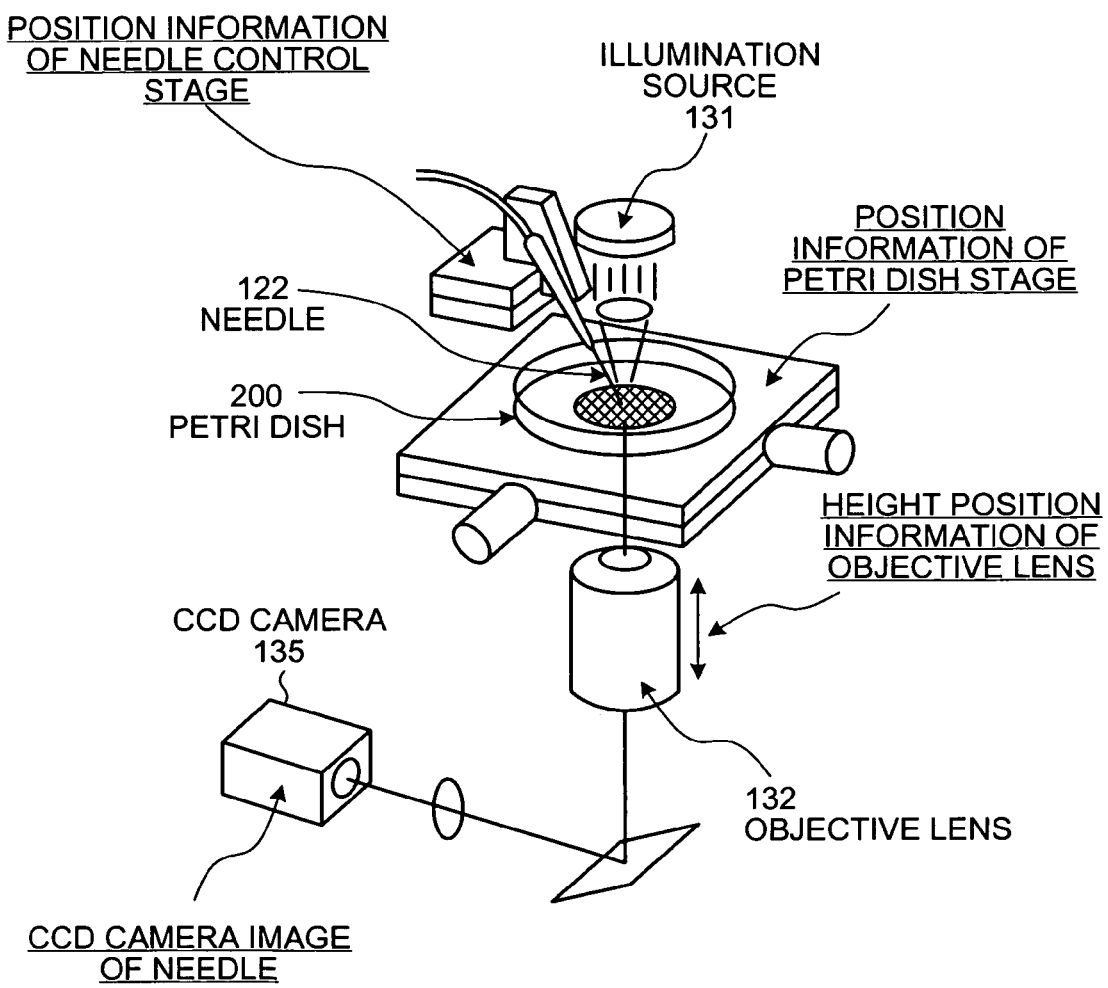
FIG. 9 is an explanatory diagram for description of the input information into the microinjection apparatus in the automatic focal point adjustment method according to the first embodiment.

Description will then be made of input information into the microinjection apparatus in the automatic focal point adjustment method according to the first embodiment. FIG. 9 is an explanatory diagram for description of input information into the microinjection apparatus in the needle position automatic adjustment method according to the embodiment. As shown in FIG. 9, the information input into the microinjection apparatus includes the position information of the petri dish stage indicating the visual field position information of the objective lens 132 in the petri dish stage on which to put the petri dish 200; the position information of the needle control stage indicating the needle control position in the needle control stage for controlling the operation of the needle 122 for the injection; the height position information of the objective lens 132 that is the information on the shift position for shifting the objective lens 132 for measuring the focal point of the adherent cell on the bottom surface of the petri dish; and the CCD camera image of the needle that is the image of the leading edge of the needle. Based on such information input into the microinjection apparatus, the output information shown in the below can be obtained.

Figure 10:
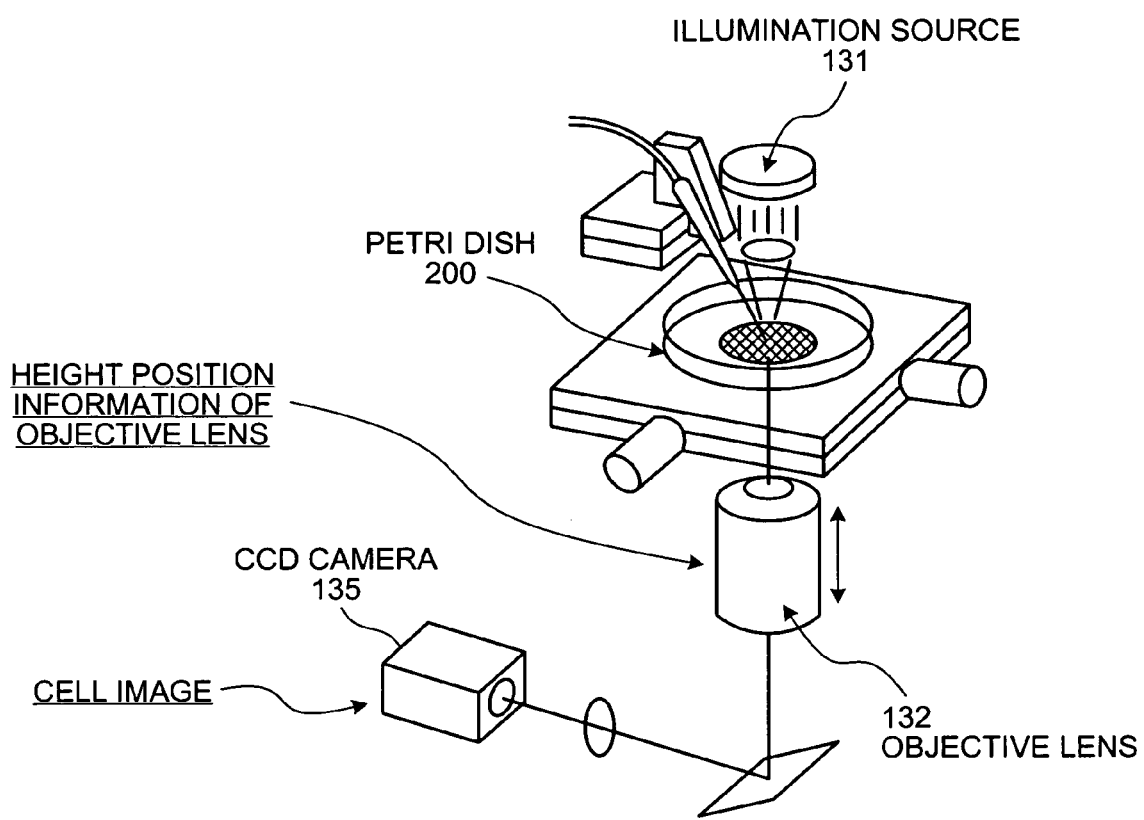
FIG. 10 is an explanatory diagram for description of the output information from the microinjection apparatus in the automatic focal point adjustment method according to the first embodiment.

Description will then be made of output information from the microinjection apparatus in the automatic focal point adjustment method according to the first embodiment. FIG. 10 is an explanatory diagram for description of output information from the microinjection apparatus in the needle position automatic adjustment method according to first the embodiment. As shown in FIG. 10, the information output by the microinjection apparatus comprises the information on the height position of the objective lens indicative of the focal position measured for obtaining a focused image of the adherent cell on the bottom surface of the petri dish 200, and cell images such as a defocused image of the adherent cell, a binarized defocused image and a focused image.

Figure 11:
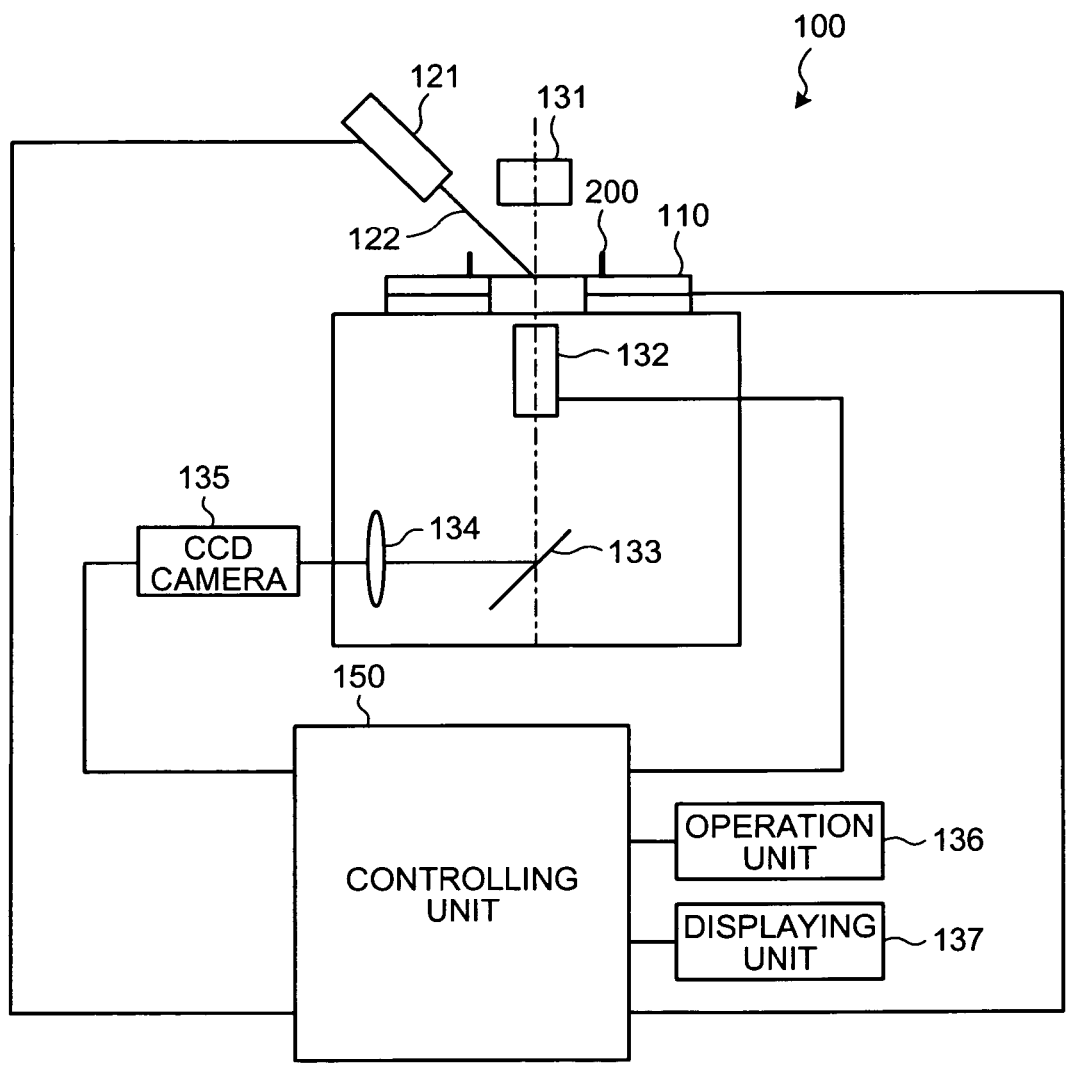
FIG. 11 is a functional block diagram of the configuration of the microinjection apparatus according to the first embodiment.

Description will then be made of configuration of the microinjection apparatus according to the first embodiment. FIG. 11 is a functional block diagram of the configuration of a microinjection apparatus 100 according to the first embodiment. The microinjection apparatus 100 includes a petri dish stage 110, an injector 121, the needle 122, the illumination source 131, the objective lens 132, a reflector 133, a focusing lens 134, a CCD (charge coupled devices) camera 135, an operation unit 136 for inputting the search parameters and petri dish information, a displaying unit 137, and a controlling unit 150.

The petri dish stage 110 is an X-Y stage movable in horizontal direction and serves as a table for holding the petri dish 200. On the petri dish stage 110, the petri dish 200 can be pressed and fixed by a force of a spring sideways. In this manner, the petri dish 200 and the petri dish stage 110 are unified as one unit, and therefore, the shifting of an observation position of the bottom surface of the petri dish for searching the adherent cell present on the bottom surface inside the petri dish corresponds with the shifting of the observation position by shifting the petri dish stage 110. The injector 121 is an apparatus for moving the needle 122 upward or downward or injecting a gene filled within the needle 122, based on the control of a needle control stage 123. The needle 122 is a capillary, glass needle with a miniaturized leading edge.

The illumination source 131 is a light source to illuminate an object of injection from above, and the objective lens 132 is a lens for obtaining a magnified image of an object of injection from below the petri dish 200. The reflector 133 is a mirror for reflecting the image obtained by the objective lens 132 toward the focusing lens 134, and the focusing lens 134 is a lens for focusing an image on an imaging device of the CCD camera 135.

The CCD camera is a means for converting an optical image to an electronic image data, using the imaging device, and it transmits the converted electronic image to the controlling unit 150.

The controlling unit 150 is a controlling unit in charge of an overall control of the microinjection apparatus 100, and performs the processing of contact detection of the needle 122 and the base surface and the injection automatic execution processing, etc. The operation unit 136 is a means for accepting the input of processing instructions and setting information necessary for the controlling unit 150 to carry out various processing. The displaying unit 137 is a means for accepting the input of instructions, etc. from users and displaying various information, and consists of a keyboard, display, etc. The displaying unit 137 is also a means for displaying the information on the state of progress of various processing and the scanned images of the adherent cell resulting from various processing.

Figure 12:
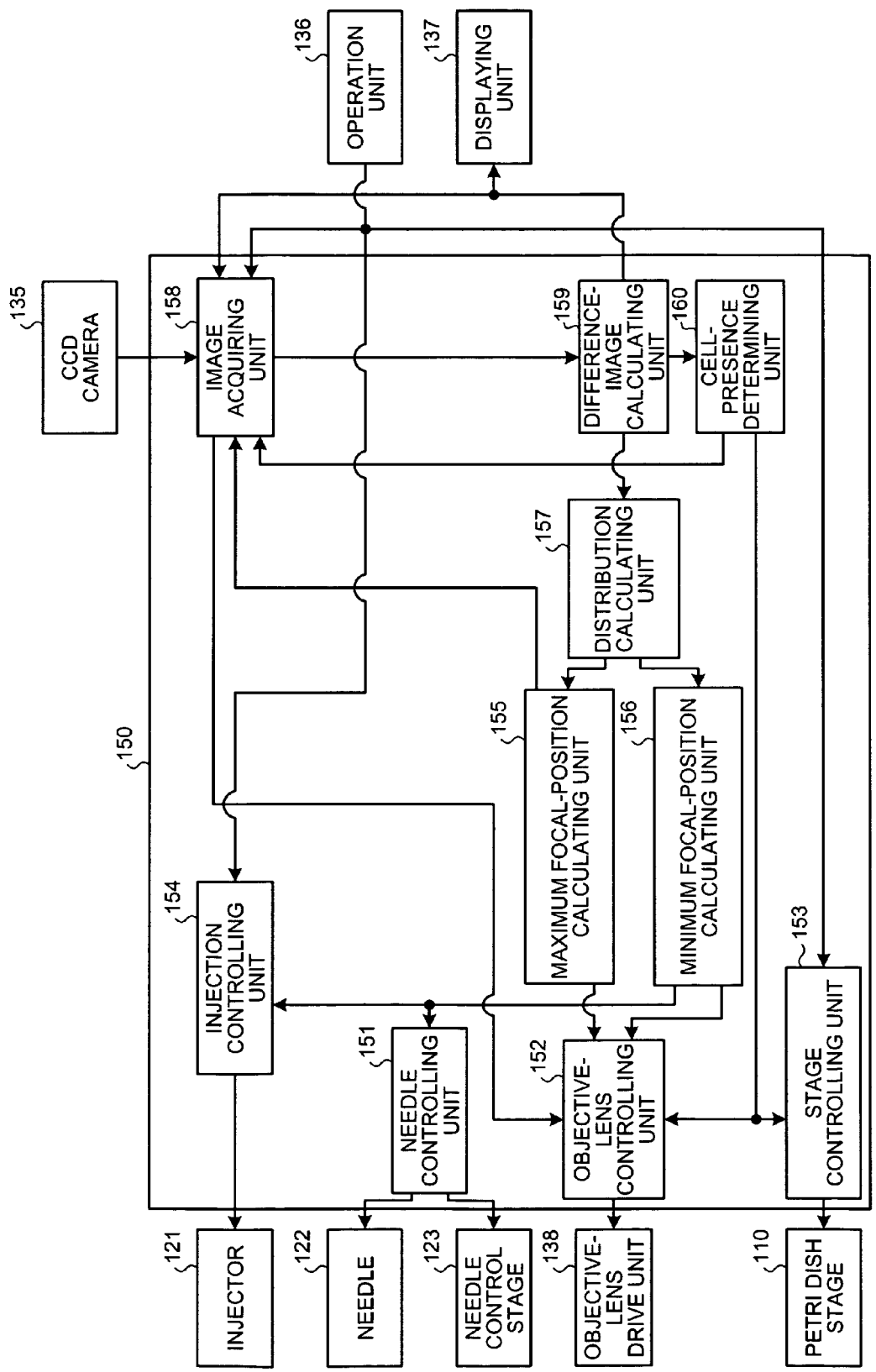
FIG. 12 is a functional block diagram of the configuration of the controlling unit of the microinjection apparatus according to the first embodiment.

Description will then be made of configuration of the controlling unit of the microinjection apparatus according to a first embodiment. FIG. 12 is a functional block diagram of the configuration of the controlling unit of the microinjection apparatus according to the first embodiment. As shown in FIG. 12, the controlling unit 150 of the microinjection apparatus includes a needle controlling unit 151 controlling the drive of the needle 122 and the needle control stage 123, an objective-lens controlling unit 152 that changes the focal position of the objective lens by controlling the drive of an objective-lens drive unit 138, a stage controlling unit 153 that controls the drive of the petri dish stage 110, an injection controlling unit 154 that controls the injector 121, a maximum focal-position calculating unit 155, a minimum focal-position calculating unit 156, a distribution calculating unit 157, an image acquiring unit 158 that acquires the image from the CCD camera 135, a difference-image calculating unit 159, and a cell-presence determining unit 160.

The image acquiring unit 158, upon receipt of an instruction to start the automatic focal point adjustment of the adherent cell accepted at the operation unit 136 or a signal input from the maximum focal-position calculating unit 155, controls the objective-lens controlling unit 152 to set the CCD focal point of the objective lens at focal positions input and set by the operation unit 136 in advance and acquires the images of the adherent cell from the CCD camera 135. The image acquiring unit 158 also transfers the reference image and images at a plurality of focal positions acquired after a sequence of processing to the difference-image calculating unit 159. The image acquiring unit 158 also outputs the images acquired in such processing to the displaying unit 137 for display.

Out of images at a plurality of focal positions, the image taken by setting the focal position, for example, 1 mm above the adherent cell is the reference image, and the image taken by setting the focal position 200 μm above the adherent cell is the image used for detecting the presence of the cell. Images taken by setting the focal point at other than these focal positions are the images to be used in a first search or a second search to be described later.

The difference-image calculating unit 159 binarizes the reference image and images at a plurality of focal positions transferred from the image acquiring unit 158, and calculates the difference images of these two images. The difference image of the image taken by setting the focal point at the focal position 200 μm above the adherent cell from the binarized and calculated reference image is transferred to the cell-presence determining unit 160. The difference images of the images taken by setting the focal point at predetermined focal positions for the first search or the second search from the binarized and calculated reference image, together with the images taken for the first or second search, are transferred to the distribution calculating unit 157. These images are output so that they can be displayed at the displaying unit 137.

The cell-presence determining unit 160, based on the difference image of the image taken by setting the focal point at the focal position 200 μm above the adherent cell from the binarized and calculated reference image, calculates an area of a region whose brightness is lower than the predetermined threshold and the minimum brightness in such a region, and judges the presence or absence of the cell in the visual field from the correlation of the area and the minimum brightness. When it is judged that the cell is present in the visual field, the cell-presence determining unit 160 instructs the objective-lens controlling unit 152 to drive an objective-lens drive unit 138 and start the shift of the focal position of the objective lens to the focal position of the first search and instructs the image acquiring unit 158 to start the acquisition of the image of the adherent cell in the first search. When it is not judged that the cell is present in the visual field, the cell-presence determining unit 160 instructs the stage controlling unit 153 to shift to the next observation site (observation position, observation point).

The state of the adherent cell as the result of the judgment of the cell-presence determining unit 160 includes not only the presence or absence of the adherent cell itself, but also the state of the adherent cell as to whether the adherent cell can become an object of the microinjection such as whether the adherent cells crowd properly, whether the adherent cell is floating, and whether the adherent cell is alive.

The distribution calculating unit 157 differentiates (i.e., calculates a differential) the difference image transferred from the difference-image calculating unit 159 and calculates an aggregate of absolute values of such differential values as a differential aggregate and calculates a differential aggregate distribution that is a distribution of the differential aggregate according to the focal positions. When the differential aggregate distribution is the distribution calculated based on the results of the first search, the differential aggregate distribution is transferred to the maximum focal-position calculating unit 155. When the differential aggregate distribution is the distribution calculated based on the results of the second search, the differential aggregate distribution is transferred to the minimum focal-position calculating unit 156.

Figure 5:
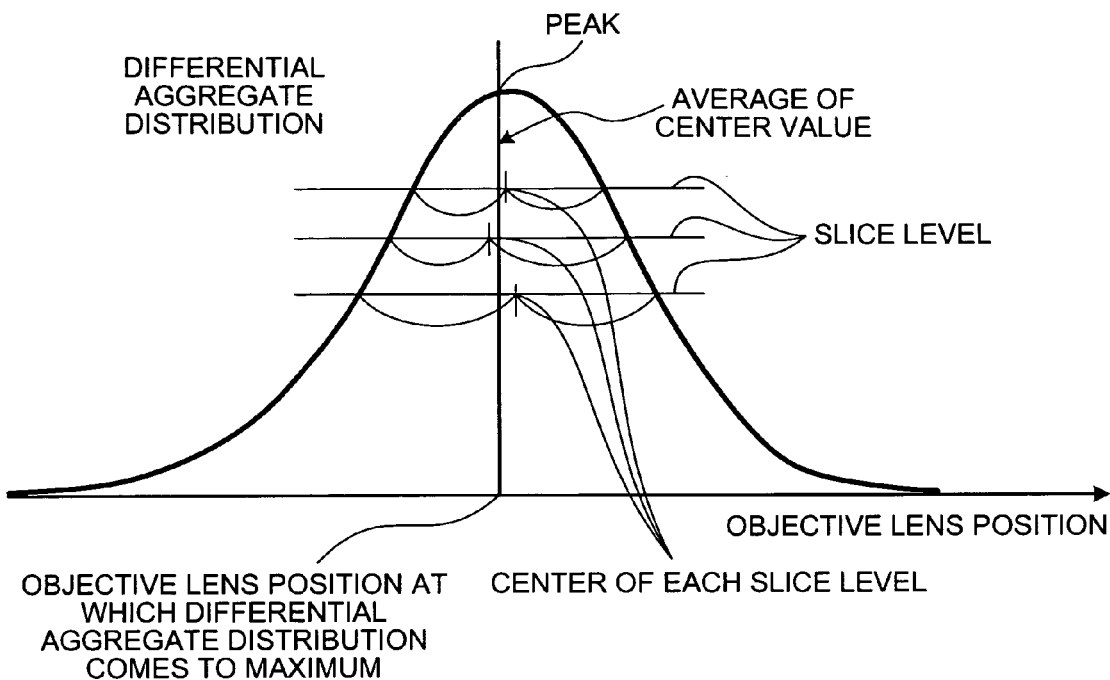
FIG. 5 is an explanatory diagram for schematic description of estimation of an objective lens position at which a differential aggregate comes to maximum in the automatic focal point adjustment method according to the first embodiment.

The maximum focal-position calculating unit 155 calculates the differential aggregate distribution maximum focal position that is the focal position at which the differential aggregate distribution assumes the maximum value, according to the method shown in FIG. 5. Thus calculated differential aggregate distribution maximum focal position is transferred to the objective-lens controlling unit 152. The objective-lens controlling unit 152 controls the drive of the objective-lens drive unit 138 so that the focal point of the objective lens 132 is shifted to the differential aggregate distribution maximum focal position as transferred.

The minimum focal-position calculating unit 156 calculates the differential aggregate distribution minimum focal position that is the focal position at which the differential aggregate distribution assumes the minimum value, according to the method shown in FIG. 6. Thus calculated differential aggregate distribution minimum focal position is transferred to the objective-lens controlling unit 152. The objective-lens controlling unit 152 controls the drive of the objective-lens drive unit 138 so that the focal point of the objective lens 132 is shifted to the differential aggregate distribution minimum focal position as transferred.

The minimum focal-position calculating unit 156 transfers the information on the calculated differential aggregate distribution minimum focal position to the needle controlling unit 151 and the injection controlling unit 154. The needle controlling unit 151 controls the needle 122 and the needle control stage 123 according to the transferred information. The injection controlling unit 154, upon receipt of the information, controls the injector 121 based on the injection operation instruction from the operation unit 136.

The stage controlling unit 153, based not only on the instruction to shift to the next observation site from the cell-presence determining unit 160, but also on the operation instruction from the operation unit 136, shifts the petri dish stage to an appropriate observation site.

Figure 13:
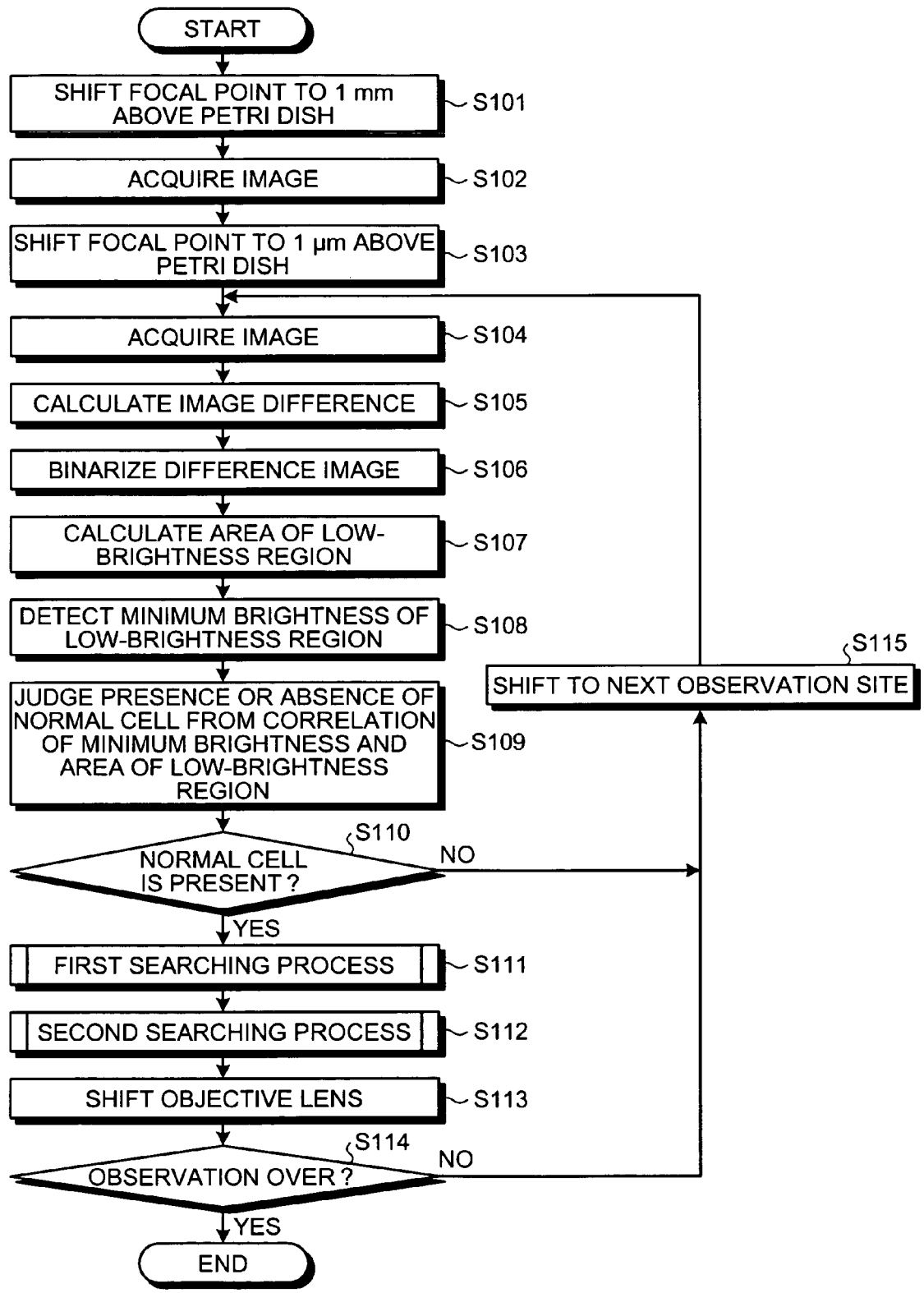
FIG. 13 is a flowchart of a procedure of the cell automatic focusing processing.

Description will then be made of a procedure of the cell automatic focusing processing performed in the microinjection apparatus according to the first embodiment. FIG. 13 is a flowchart of a procedure of the cell automatic focusing processing. As shown in FIG. 13, the focal position is shifted to the position 1 mm above the petri dish 200 (step S101), and an image as a reference image is acquired at this focal position (step S102). The focal position is further shifted to the position 200 μm above the petri dish 200 (step S103), and an image is acquired at this focal position (step S104).

The difference image is calculated of the reference image acquired at step S102 and the image acquired at step S104 (step S105), and the difference image is binarized (step S106). Calculation is made of an area of the low-brightness region whose brightness is lower than the threshold contained in the binarized difference image (step S107), and the minimum brightness in the low-brightness region is detected (step S108). Judgment is made as to the presence or absence of a normal cell suitable for the microinjection in the visual field, from the correlation of minimum brightness and the area of the low-brightness region (step S109).

Judgment is made as to whether the normal cell is present (step S110), and if it is judged that the normal cell is present (step S110: Yes), then the first search process is executed (step S111) and the second processing is executed (step S112). Then the objective lens 132 is shifted to the focal position of the objective lens measured by the second search process at the step S112 (step S113). Judgment is then made as to whether the observation is finished (step S114), and if the observation is finished (step S114: Yes), then the cell automatic focusing processing is finished. If the observation is not yet finished (step S114: No), then the process goes to the step S115.

At step S110, even if it is not judged that the normal cell is present (step S110: No), the process goes to the step S115. At step S115, the petri dish stage 110 is controlled and driven to be shifted to a next observation site. If the step S115 is finished, the process goes to the step S104.

Execution of such sequence of processing makes it possible to automatically search for and detect an observation point at which the adherent cell is present within the visual field of the objective lens 132. Namely, there is no need for the trial and error of manually adjusting so that the adherent cell comes within the visual field of the objective lens 132 by manually shifting the position of the petri dish 200 or shifting the position of the adherent cell itself on the bottom surface of the petri dish 200, and the focal position of the cell can be grasped, and the focal point can be adjusted, without complicated work and more accurately, and the operation of the microinjection can be performed more efficiently. Furthermore, the automatic execution of the above-identified sequence of processing permits the reduction of psychological burden and psychological fatigue at the time of microinjection.

Description will then be made of the first search process executed in the microinjection apparatus according to the first embodiment. FIG. 14 is a flowchart of a procedure of the first search process shown at the step S111 of FIG. 13. As shown in FIG. 14, the objective lens 132 is shifted over the range of ±200 μm at 20 μm pitch (focal point interval) (step S121). The focal position as a basis of ±200 μm is the 200 μm that was set at the step S103 of the cell automatic focusing processing.

Next, an image is acquired at each focal position of the objective lens 132 shifted at 20 μm pitch at step S121 (step S122). Then, calculation is made of a difference image of the reference image acquired at the step S102 of the cell automatic focusing processing and the image at each focal position acquired at the step S122 (step S123). Then, calculation is made of a differential aggregate distribution based on differential values of each difference image (step S124), and the objective lens position at which the differential aggregate distribution assumes the maximum value is detected (step S125).

Description will then be made of the second search process executed in the microinjection apparatus according to the first embodiment. FIG. 15 is a flowchart of a procedure of the second search process shown at the step S112 of FIG. 13. As shown in FIG. 15, the objective lens 132 is shifted over the range of ±20 μm at 1 μm pitch (step S131). The focal position as a basis of ±20 μm is the focal position determined by the objective lens position detected at the step S125 of the first search process.

Next, an image is acquired at each focal position of the objective lens 132 shifted at 1 μm pitch at step S131 (step S132). Then, calculation is made of a difference image of the reference image acquired at the step S102 of the cell automatic focusing processing and the image at each focal position acquired at the step S132 (step S133). Then, calculation is made of a differential aggregate distribution based on differential values of each difference image (step S134), and a best-focus objective-lens-position calculation process is performed (step S135).

Figure 16:
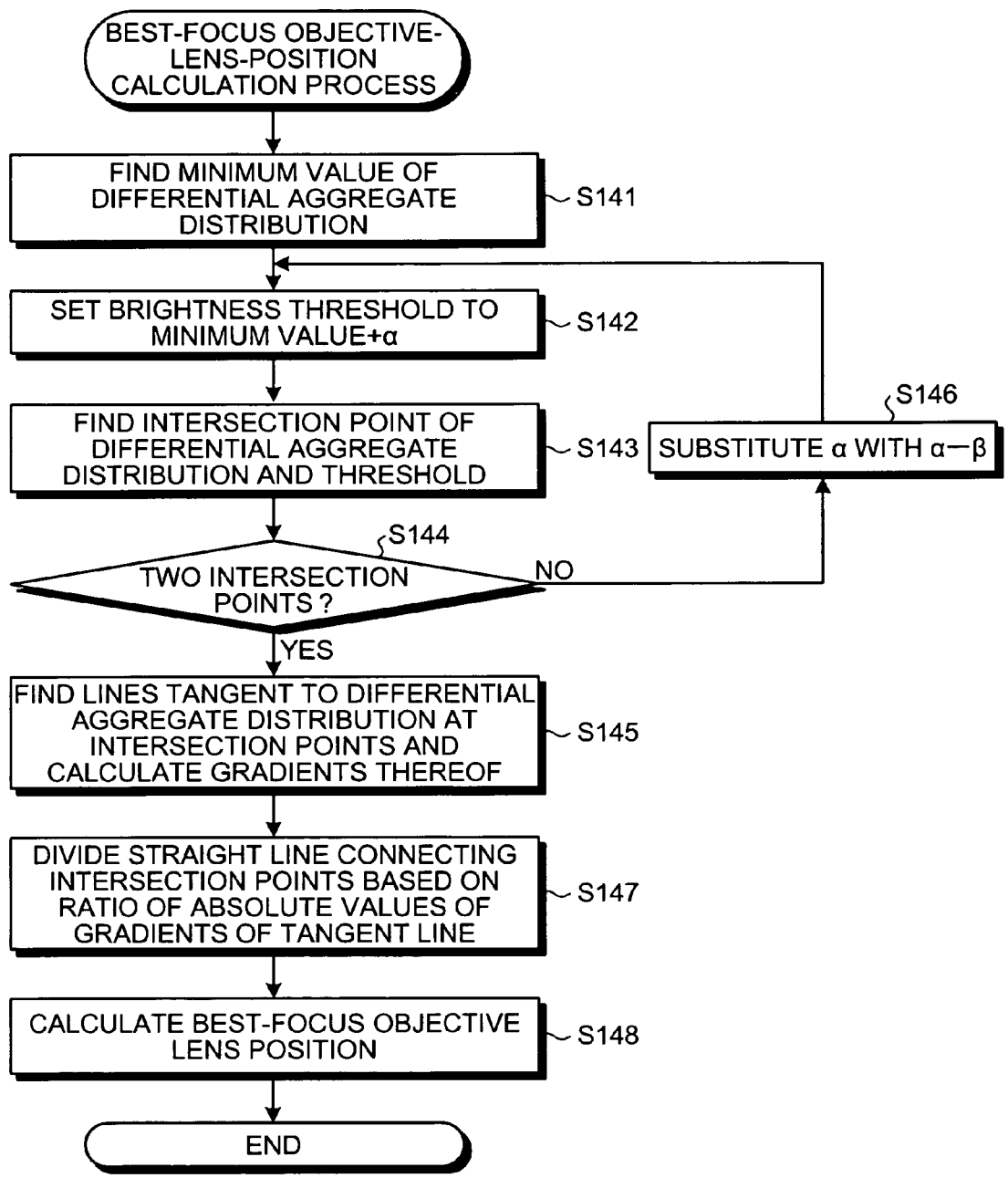
FIG. 16 is a flowchart of a procedure of the best-focus objective-lens-position calculation process.

Description will then be made of the best-focus objective-lens-position calculation process executed in the microinjection apparatus according to the first embodiment. FIG. 16 is a flowchart of a procedure of the best-focus objective-lens-position calculation process shown at the step S135 of FIG. 15. As shown in FIG. 16, a minimum value of the differential aggregate distribution is obtained (step S141), and a threshold of brightness is set at the value (minimum value+α) obtained by adding a predetermined value α to the minimum value (step S142). The next step is to obtain points at the intersection of the differential aggregate distribution curve with the threshold set at the step S142 (step S143).

Judgment is made as to whether there are two points at the intersection of the differential aggregate distribution with the threshold set at the step S142 (step S144). If it is judged that two intersection points are present (step S144: Yes), then lines tangent to the differential aggregate distribution curve at these intersection points are obtained and gradients thereof are calculated (step S145). Then, the line segment connecting the intersection points are divided at the ratio of absolute values of gradients of the tangent lines calculated at the step S145 (step S147). Then, with respect to the point at which the line segment is divided at the step S147, such component of this point that relates to the objective lens position is obtained and is determined as the best-focus objective lens position (step S148).

On the other hand, if it is not judged at the step S144 that two intersection points are present (step S144: No), then α that defines the threshold set at the step S142 is substituted by α−β (constantly α>β; β is a constant value) (step S146), and the process goes to the step S142. In this manner, α is made smaller step by step until two intersection points are present, and ultimately, it comes to be judged that two intersection points are present.

Second Embodiment

Figure 17:
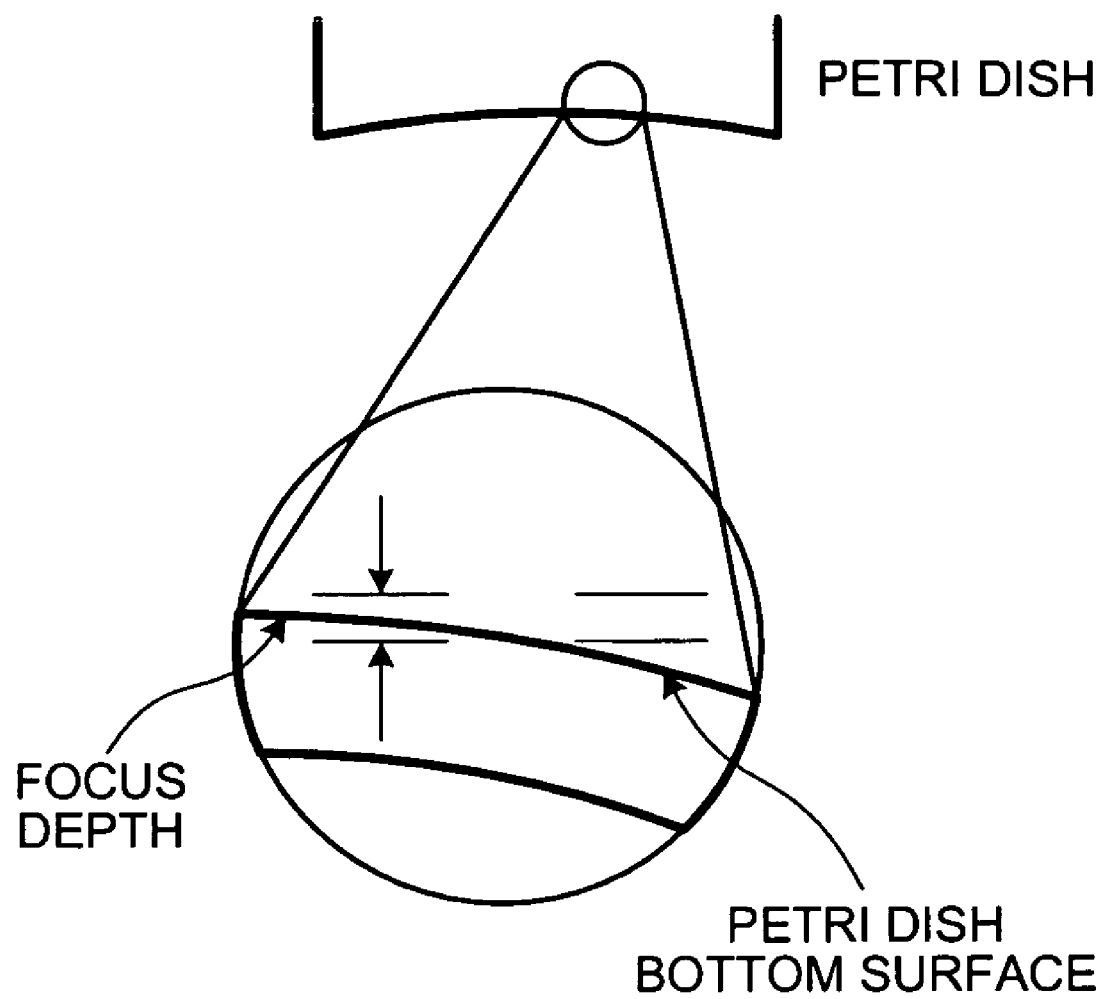
FIG. 17 is an explanatory diagram for schematic description of the inclination of the petri dish bottom surface.

Description will now be made of a petri dish inclination calculation method in a microinjection apparatus of a second embodiment of the present invention, with reference to FIGS. 17 to 20. The second embodiment is practiced utilizing the first embodiment. Firstly, schematic description will be made of an inclination of a bottom surface of a petri dish as a premise of the second embodiment, with reference to FIG. 17. FIG. 17 is an explanatory diagram for schematic description of the inclination of the petri dish bottom surface.

As shown in FIG. 17, the bottom surface of the petri dish is not completely horizontal, but has an inclination in such manner that the bottom surface is more elevated at the center of the petri dish. The inclination of the petri dish has, for example, a height difference of 10 μm in vertical direction relative to a difference of 1 mm in horizontal direction. Therefore, even if a focus depth (focal position) corresponds to the bottom surface at a certain visual field position, a slightest slip of the visual field position causes the focus depth to depart from the bottom surface of the petri dish, ruining the accuracy of the precise adherent cell observation. Especially, it is a problem that when the leading edge of the needle for injection collides with the bottom surface, it damages the leading edge of the needle, and a constant distance must always be kept from the bottom surface, irrespective of the inclination of the bottom surface of the petri dish.

Accordingly, the invention of the second embodiment was conceived with an object of automatically measuring the inclination of the bottom surface of the petri dish, using the automatic focal point adjustment method shown in the first embodiment, and enabling the leading edge of the needle to automatically and always keep a constant distance from the bottom surface along thus measured inclination of the bottom surface of the petri dish, irrespective of the position on or inclination of the bottom surface of the petri dish.

Figure 18:
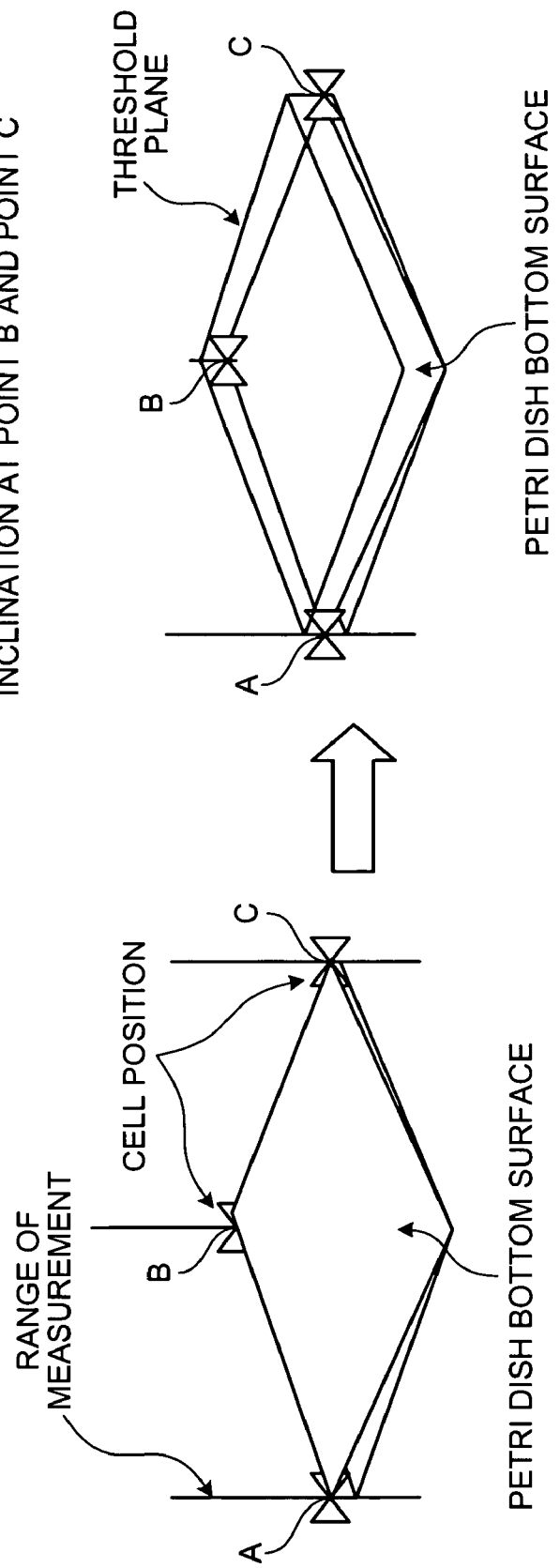
FIG. 18 is an explanatory diagram for schematic description of the petri dish bottom surface inclination calculation process according to a second embodiment of the present invention.

Schematic description will then be made of a petri dish bottom surface inclination calculation process according to the second embodiment. FIG. 18 is an explanatory diagram for schematic description of the petri dish bottom surface inclination calculation process according to the second embodiment. As shown in FIG. 18, since a first search and a second search are performed for all of the cells positioned at three selected points of positions of A to C, it took time to search for focal positions of all cells in view of the fact that the first search, as compared with the second search, requires a wider range of measurement for focal position of an objective lens.

However, the second embodiment is so designed that the first search and the second search are performed for a cell positioned at one particular point (point A in second embodiment) and only the second search is performed for cells positioned at two other points (point B and point C in second embodiment) to search for a degree of inclination of the petri dish. As a result, the range of measurement of the focal position of the objective lens can be limited and the time for searching for focal positions of all cells can be shortened. Points A to C in the second embodiment are referred to as "petri dish bottom surface inclination measurement point" or simply as "measurement point".

Figure 19:
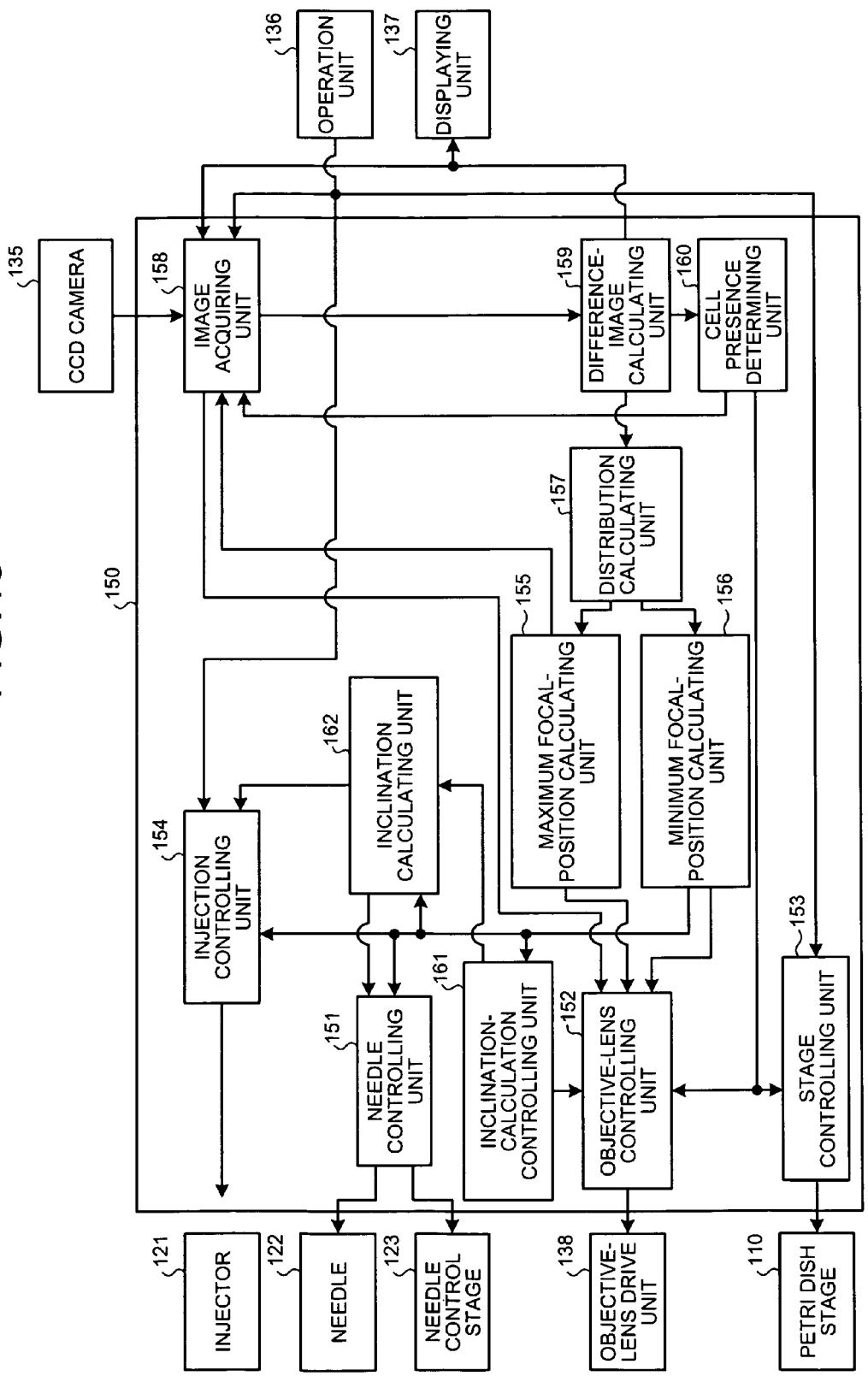
FIG. 19 is a functional block diagram of the configuration of the controlling unit of the microinjection apparatus according to the second embodiment.

Description will then be made of a configuration of the microinjection apparatus according to the second embodiment. FIG. 19 is a functional diagram of the configuration of the microinjection apparatus according to the second embodiment. A functional configuration of the microinjection apparatus 100 of the second embodiment is the functional configuration of the microinjection apparatus 100 of the first embodiment with an addition of the following functional blocks. Namely, the microinjection apparatus 100 of the second embodiment has an inclination-calculation controlling unit 161 and an inclination calculating unit 162 in addition.

The inclination-calculation controlling unit 161, upon receipt of the information on a minimum focal position calculated by the minimum focal-position calculating unit 156, instructs the inclination calculating unit 162 to calculate the petri dish bottom surface inclination. The inclination calculating unit 162, upon receipt of the instruction to calculate the bottom surface inclination, calculates the inclination of the bottom surface of the petri dish, based on the petri dish inclination minimum focal position at each petri dish bottom surface inclination calculation point calculated by the minimum focal-position calculating unit 156. Thus calculated inclination of the bottom surface of the petri dish is transferred from the inclination calculating unit 162 to the needle controlling unit 151. The needle controlling unit 151, based on the inclination of the bottom surface of the petri dish, controls the needle control stage so that the leading edge of the needle keeps a constant distance (for example 1 μm) from the bottom surface of the petri dish, so as not to contact the bottom surface of the petri dish.

Figure 20:
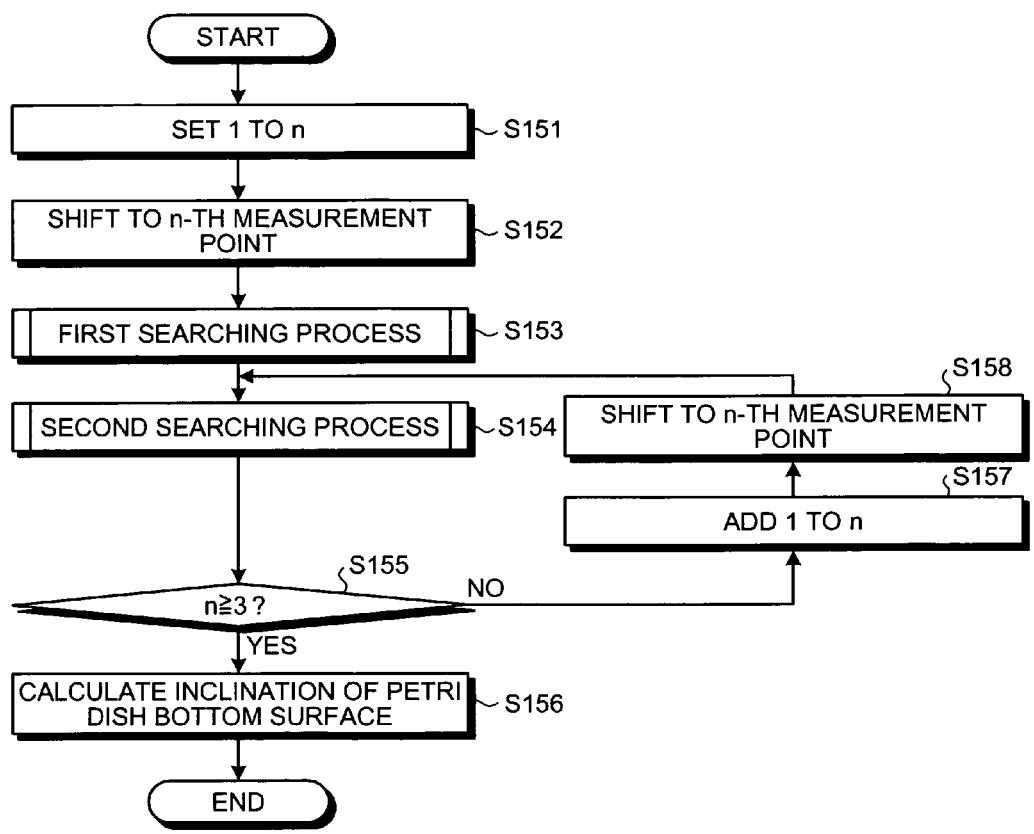
FIG. 20 is a flowchart of a procedure of a petri dish bottom surface inclination calculation process.

Description will then be made of a petri dish bottom surface inclination calculation process. FIG. 20 is a flowchart of a procedure of the petri dish bottom surface inclination calculation process. As shown in FIG. 20, a counter variable n (n is a natural number) is set to 1 (step S151), and the petri dish stage 110 is controlled to be shifted to the n-th measurement point (step S152).

Next, the first search process is performed (step S153), and the second search process is performed (step S154). The first search process and the second search process are as shown in the first embodiment. Then, judgment is made as to whether $n \geq 3$ applies (step S155). If it is judged that $n \geq 3$ applies (step S155: Yes), then calculation is made of the inclination of the bottom surface of the petri dish (step S156). On the other hand, if it is not judged that $n \geq 3$ applies (step S155: No), then 1 is added to n (step S157) and the petri dish stage is controlled to shift to the n-th measurement point (step S158).

Execution of such sequence of processing makes it possible to automatically measure the inclination of the bottom surface of the petri dish, and enable the leading edge of the needle to automatically and always keep a constant distance from the bottom surface along thus measured inclination of the bottom surface of the petri dish, irrespective of the position on or inclination of the bottom surface of the petri dish. Therefore, the microinjection work can be performed, with no worry about a possible breakage of the leading edge of the needle by its contact with the bottom surface of the petri dish 200, more accurately, more efficiently, and more safely. Furthermore, no necessity of worrying about a possible breakage of the leading edge of the needle by its contact with the bottom surface of the petri dish 200 permits the reduction of psychological burden and psychological fatigue at the time of microinjection.

While the first embodiment and the second embodiment of the present invention are described above, the present invention is not limited thereto or thereby. Within the scope of the technological idea described in the scope of the claim, the present invention may be embodied by further varied, different embodiments. The effects of the present invention are not limited to those described in the first embodiment and the second embodiment.

Specifically, the configuration and function blocks of the microinjection apparatus 100 and the controlling unit 150 thereof illustrated in the above-identified first embodiment and second embodiment are illustrated only as an example, and to realize the microinjection apparatus and the automatic focal point adjustment method described in the scope of claim, the configuration and function blocks of the microinjection apparatus 100 and the controlling unit 150 thereof can be changed without departing from the scope of the claim.

The embodiments achieve an effect of being able to measure a state of a cell without involving human work and being able to confirm the state of the cell in performing a microinjection, without a necessity of experienced skill, efficiently, and simply.

The embodiments also achieve an effect of being able to detect the focal position more efficiently and more accurately since, after detecting a first focal position at a first focal point interval, detection is made of a second focal position at a second focal point interval narrower than the first focal point interval within a predetermined range including the first focal position, namely, the second focal position is precisely detected after the first focal position is roughly detected.

The embodiments also achieve an effect of being able to calculate an inclination of a base surface only by detecting the focal position of the cell at least at three positions, permitting a simpler and speedier calculation of the inclination of the base surface.

The embodiments also achieve an effect of being able to avoid an accident of a needle colliding with a base surface even if an observation position changes by keeping a constant distance between the base surface and a leading edge of the needle according to an inclination of the base surface, irrespective of the observation position.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A microinjection apparatus that injects an object into a cell on a base surface with a needle, the microinjection apparatus comprising:
an image acquiring unit that acquires a plurality of images of the cell at different focal positions;
a state deciding unit that decides a state of the cell based on a difference image obtained from a first image and a second image included in the plurality of images;
a first focal position detecting unit that detects a first focal position of the image acquiring unit at which a differential aggregate distribution according to focal positions of a first focal point interval assumes a maximum value as calculated based on difference images obtained from the first image and images of the cell acquired by the image acquiring unit at the focal positions of the first focal point interval, at an observation position on the base surface at which the state of the cell is measured by the state deciding unit; and
a second focal position detecting unit that detects a second focal position of the image acquiring unit at which a differential aggregate distribution according to focal positions of a second focal point interval assumes a minimum value as calculated based on difference images obtained from the first image and images of the cell acquired by the image acquiring unit at the focal positions of the second focal point interval narrower than the first focal point interval, at the observation position, each of the focal positions of the second focal point interval being within a predetermined range from the first focal position detected by the first focal position detecting unit.

2. The microinjection apparatus according to claim 1, wherein the state deciding unit decides the state of the cell based on a brightness of the difference image.

3. The microinjection apparatus according to claim 2, wherein the state deciding unit decides the state of the cell based on a correlation of areas in the difference image having brightness lower than a threshold and higher than the threshold.

4. The microinjection apparatus according to claim 2, wherein the state of the cell includes at least one of presence or absence of the cell, life or death state of the cell, and adherent state of the cell.

5. The microinjection apparatus according to claim 1, further comprising an inclination calculating unit that calculates an inclination of the base surface based on the second focal position and the first focal position at least at three observation positions on the base surface.

6. The microinjection apparatus according to claim 5, further comprising a distance keeping unit that keeps a constant distance between the base surface and a leading edge of the needle, irrespective of the observation positions, according to calculated inclination of the base surface.

7. A method of automatically adjusting a focal point of a lens relative to a cell for injecting an object into the cell with a needle, the method comprising:

acquiring with an image acquiring unit a plurality of images of the cell at different focal positions;

deciding a state of the cell based on a difference image obtained from a first image and a second image included in the plurality of images;

first detecting including detecting a first focal position of the image acquiring unit at which a differential aggregate distribution according to focal positions of a first focal point interval assumes a maximum value as calculated based on difference images obtained from the first image and images of the cell acquired by the image acquiring unit at the focal positions of the first focal point interval, at an observation position on the base surface at which the state of the cell is decided at the deciding; and second detecting including detecting a second focal position of the image acquiring unit at which a differential aggregate distribution according to focal positions of a second focal point interval assumes a minimum value as calculated based on difference images obtained from the first image and images of the cell acquired by the image acquiring unit at the focal positions of the second focal point interval narrower than the first focal point interval, at the observation position, each of the focal positions of the second focal point interval being within a predetermined range from the first focal position detected by the first detecting.

8. The method according to claim 7, wherein the deciding includes deciding the state of the cell based on a brightness of the difference image.

9. The method according to claim 8, wherein the deciding includes deciding the state of the cell based on a correlation of areas in the difference image having brightness lower than a threshold and higher than the threshold.

10. The method according to claim 8, wherein the state of the cell includes at least one of presence or absence of the cell, life or death state of the cell, and adherent state of the cell.

11. The method according to claim 7, further comprising calculating an inclination of the base surface based on the second focal position and the first focal position at least at three observation positions on the base surface.

12. The method according to claim 11, further comprising keeping a constant distance between the base surface and a leading edge of the needle, irrespective of the observation positions, according to calculated inclination of the base surface.

* * * * *